(12) United States Patent
Nishiyama et al.

(10) Patent No.: US 7,499,157 B2
(45) Date of Patent: Mar. 3, 2009

(54) SYSTEM FOR MONITORING FOREIGN PARTICLES, PROCESS PROCESSING APPARATUS AND METHOD OF ELECTRONIC COMMERCE

(75) Inventors: Hidetoshi Nishiyama, Fujisawa (JP); Minori Noguchi, Mitsukaido (JP); Tetsuya Watanabe, Honjo (JP); Takuaki Sekiguchi, Honjo (JP)

(73) Assignee: Hitachi Electronics Engineering Co, Ltd., Tokyo (JP)

( * ) Notice: Subject to any disclaimer, the term of this patent is extended or adjusted under 35 U.S.C. 154(b) by 0 days.

(21) Appl. No.: 11/727,037

(22) Filed: Mar. 23, 2007

(65) Prior Publication Data

US 2007/0165212 A1   Jul. 19, 2007

Related U.S. Application Data

(63) Continuation of application No. 10/630,734, filed on Jul. 31, 2003, now Pat. No. 7,196,785.

(30) Foreign Application Priority Data

Aug. 2, 2002   (JP) ............................. 2002-225692

(51) Int. Cl.
  *G01N 21/00* (2006.01)
(52) U.S. Cl. ................................. 356/237.4; 356/237.3
(58) Field of Classification Search .............. 356/237.1, 356/237.2, 237.3, 237.4, 237.5
  See application file for complete search history.

(56) References Cited

U.S. PATENT DOCUMENTS

| 5,233,191 | A | | 8/1993 | Noguchi et al. |
| 5,463,459 | A | | 10/1995 | Morioka et al. |
| 5,858,863 | A | * | 1/1999 | Yokoyama et al. ........... 438/514 |
| 5,973,785 | A | * | 10/1999 | Okamoto ..................... 356/521 |
| 6,650,409 | B1 | * | 11/2003 | Noguchi et al. ........... 356/237.3 |
| 6,894,773 | B2 | * | 5/2005 | Morioka et al. .......... 356/237.5 |

FOREIGN PATENT DOCUMENTS

| JP | 05-218163 | 8/1993 |
| JP | 05-259259 | 10/1993 |
| JP | 06-258239 | 9/1994 |
| JP | 06-275688 | 9/1994 |
| JP | 08-145900 | 6/1996 |
| JP | 08-250385 | 9/1996 |
| JP | 08-250569 | 9/1996 |

* cited by examiner

*Primary Examiner*—Roy M Punnoose
(74) *Attorney, Agent, or Firm*—Antonelli, Terry, Stout & Kraus, LLP.

(57) ABSTRACT

A system for monitoring foreign matter includes a manufacturing line having plural process processing apparatuses, a production management system which manages the processing of workpieces in the manufacturing line, plural optical heads which monitor foreign matter in relation to at least one of the workpieces, and which provide an output signal indicative thereof, and at least one image signal processing unit provided in a lesser number than a number of the plural optical heads for processing the output signal therefrom.

3 Claims, 33 Drawing Sheets

WHOLE WAFER SURFACE INSPECTION

PIXEL SIZE REDUCED

(a) WAFER PROCESS DATA (b) LAYOUT DATA ON WAFER (c) INSPECTION REQUIREMENTS DATA ON PRODUCTION APPARATUS AND COMPACT FOREIGN MATTER MONITOR (d) INSPECTION REFERENCE IMAGE DATA —216

(e) INSPECTION RECIPE DATA
   ((e-1) THRESHOLD FOR JUDGMENT, (e-2) QUANTITY OF ILLUMINATION LIGHT, (e-3) INSPECTION AREA, (e-4) INSPECTION METHOD (XY SCAN, ROTARY SCAN), ETC.)

(f) INSPECTION RESULT DATA (g) DEFECTIVE AREA IMAGE DATA (h) FAILURE ANALYSIS REFERENCE DATA
   (FOREIGN MATTER DISTRIBUTION DATA)

① COMPACT FOREIGN MATTER MONITOR (OPTICAL HEAD) ON / OFF MONITOR FUNCTION

② SIGNAL PROCESSING TIMING CONTROL (INPUT / OUTPUT CONTROL) FUNCTION

③ INSPECTION RECIPE PREPARE FUNCTION

④ IDENTIFICATION CODE RECOGNIZE FUNCTION

⑤ INSPECTION RECIPE SELECT FUNCTION

⑥ ALARM OUTPUT FUNCTION

⑦ COMPACT FOREIGN MATTER MONITOR OPTICAL HEAD MAINTENANCE MANAGEMENT FUNCTION
   (FOR EXAMPLE, REPLACEMENT MANAGEMENT OF LIGHT SOURCE EVERY n WAFERS INSPECTED)

FIG. 27

EQUIPMENT NAME: A A A ▼   LOT NO.: D D D ▼   Status: — JUDGE BY INSPECTION RESULT
PRODUCT NAME: B B B ▼
PROCESS NAME: C C C ▼

OCCURRENCE OF ABNORMALITY (DAMAGE BY ARM) — 271

SLOT: 1 — INSPECTION RESULT
SLOT: 2
SLOT: 3
SLOT: 4
SLOT: 5 — INSPECTION RESULT OF DEFECTIVE WAFER

SLOT: 6
SLOT: 7
SLOT: 8
SLOT: 9
SLOT: 10

SYSTEM FOR MONITORING FOREIGN PARTICLES, PROCESS PROCESSING APPARATUS AND METHOD OF ELECTRONIC COMMERCE

CROSS REFERENCE TO RELATED APPLICATION

This is a continuation of U.S. application Ser. No. 10/630,734, filed Jul. 31, 2003, now U.S. Pat. No. 7,196,785, the contents of which are incorporated herein by reference.

BACKGROUND OF THE INVENTION

The present invention relates to a system for monitoring foreign matter (foreign particles) where its base system collectively receives and processes foreign matter detection signals from foreign matter monitoring optical heads mounted in many process processing apparatuses (many process processing apparatuses) forming a manufacture line of semiconductors or the like, a process processing apparatus and an electronic transaction method (a method of electronic commerce) using the system for monitoring foreign matter.

There are known conventional techniques concerning foreign matter monitoring systems as disclosed in Japanese Patent Laid-Open Nos. 5-218163 (corresponding to U.S. Pat. No. 5,463,459) (Prior Art 1), 6-258239 (Prior Art 2), 8-250385 (corresponding to U.S. application Ser. No. 08/617,270) (Prior Art 3), 8-250569 (corresponding to U.S. application Ser. No. 08/617,270) (Prior Art 4).

In Prior Arts 1 and 2, an inline foreign matter monitor system is described. In this case, compact foreign matter monitors are set up in the inlets/outlets of process processing apparatuses or in transport areas between process processing apparatuses in a volume production semiconductor manufacture process line and a foreign matter control system takes in foreign matter data from the compact foreign matter monitors to provide foreign matter control on a single wafer basis. In Prior Arts 3 and 4, an on-machine foreign matter monitor system is described. In this system, a process processing apparatus has a foreign matter monitor mounted therein to measure foreign matters sticking to works before and after they are processed therein so that foreign matters sticking to works are under control on an each lot or work basis and, based on the result of measurement, it is determined whether works supplied into the process processing apparatus should be stopped or not.

Technique disclosed in Japanese Patent Laid-Open No. 8-145900 (Prior Art 5) is known as a conventional technique for compact foreign matter monitors. According to Prior Art 5, compact foreign matter monitors are placed where they are accessible by the arms of robots which are fixed between a vacuum process room and a loader and between a vacuum process room and an unloader. In addition, a vacuum process apparatus is described in Japanese Patent Laid-Open No. 5-259259 (Prior Art 6). A vacuum process apparatus according to this prior art has a load lock room to relay a workpiece, a process room to process a workpiece, an inspection room having a foreign matter monitor installed therein and a platform having transport means to transfer a workpiece among the load lock room, process room and inspection room.

In Japanese Patent Laid-Open No. 6-275688 (Prior Art 7), failure analysis technique is described. According to this prior art for semiconductor wafers and the like, a foreign matter inspection apparatus, an appearance inspection apparatus and a probing inspection apparatus are connected to an appearance failure analysis apparatus via each analysis station and a product design support system and a data input terminal are connected to the appearance failure analysis apparatus. To clarify a causal relationship, the apparatus failure analysis apparatus compares the fail bit data acquired from the probing inspection apparatus with the appearance defect information acquired from the appearance inspection apparatus.

SUMMARY OF THE INVENTION

Recent semiconductor chips, as represented by system LSIs, contain a great number of functional circuit blocks formed by very fine circuit patterns and they are becoming expensive more and more. Further, semiconductor wafers having arrays of these chips are becoming larger and more expensive. To improve the yield from a semiconductor device manufacture process line, it is therefore very important to find a dusting source as early as possible (with a limited number of wafers influence) if any in the manufacture line in order to prevent the dusting from causing mass failure.

In addition, each semiconductor wafer goes through so many manufacture processes (including such common manufacture processes as photo process, film deposition process, etching process and CMP process) until it is completed. On the other hand, a major cause of bad semiconductor wafers is foreign matters which occur in individual process machines (etching, sputtering, CVD, exposure and other processing apparatus) and stick onto wafers therein. Basically, foreign matters do not stick to semiconductor wafers while they are carried between process machines since they are accommodated in cassettes which provides clean ambience to semiconductor wafers. Therefore, on-machine foreign matter monitors are needed to detect foreign matters which stick to semiconductor wafers in individual process processing apparatuses as described in Prior Arts 3 and 4.

However, although a foreign matter monitor system according to Prior Arts 3 and 4 comprises compact and inexpensive foreign matter monitors mounted in a great number of process processing apparatuses which constitutes a semiconductor manufacture line, its system configuration is not given sufficient consideration as part of the semiconductor manufacture line.

It is a first object of the present invention to provide a system for monitoring foreign matter (foreign particles) which comprises compact and inexpensive foreign matter monitors mounted in a great number of main process processing apparatuses constituting a manufacture line of semiconductors or the like and is optimized comprehensively as part of the manufacture line.

It is a second object of the present invention to provide a process processing apparatus optimized to install a compact foreign matter monitor.

It is a third object of the present invention to provide an electronic transaction method (a method of electronic commerce) using a foreign matter monitor system.

According to an aspect of the present invention, there is provided a system for monitoring foreign matter comprising: a manufacture line having plural process processing apparatuses; a production management system which manages the processing of workpieces in the manufacture line; foreign matter monitors mounted as on-machine equipment in said plural process processing apparatuses, said foreign matter monitors each having: an optical head containing a detecting optical system for irradiating a workpiece with light and a detecting optical system for receiving reflected and scattered light from the workpiece and converting the received light to a detection image signal; and an A/D converter for converting the detection image signal, which is obtained through conversion by the detecting optical system, to a detection digital image signal; and a base system having: a control unit for acquiring control information including information identifying each foreign matter monitor, process processing information and workpiece information, the process processing information and the workpiece information being acquired from the production management system; a buffer memory for storing said detection digital image signal, which is acquired from each foreign matter monitor, in association with the corresponding foreign matter monitor; a database storing inspection recipes each associated with a foreign matter monitor; and an image signal processing unit used for, based on a detection digital image signal associated with a foreign matter monitor and acquired from the buffer memory, judging whether foreign matter and other defects are present on a workpiece according to an inspection recipe which is selected for the corresponding foreign matter monitor based on control information from the control unit.

According to an embodiment of the present invention, there is provided a foreign matter monitoring system as described above and characterized in that each of said main plural process processing apparatuses comprises: a process room to process workpieces; a cassette room where a cassette containing a workpiece is carried in and out; and a platform providing clean ambience to the workpiece for transportation between the process room and the cassette room.

According to an embodiment of the present invention, there is provided a foreign matter monitoring system as described above and characterized in that an optical head for the foreign matter monitor is set up in said platform.

According to an embodiment of the present invention, there is provided a foreign matter monitoring system as described above and characterized in that each of said main plural process processing apparatuses comprises: a process room to process workpieces; a cassette room where a cassette containing a workpiece is carried in and out; a platform providing clean ambience to the workpiece for transportation between the process room and the cassette room; and a small clean environment room.

According to an embodiment of the present invention, there is provided a foreign matter monitoring system as described above and characterized in that an optical head for the foreign matter monitor is set up in said small clean environment room and said clean ambience is kept clean to class 20 or better.

According to an embodiment of the present invention, there is provided a foreign matter monitoring system as described above and characterized in that said image signal processing unit in said base system is configured so as to prepare a defect distribution map over a workpiece for each foreign matter monitor, said base system further comprises a data analysis processing unit which performs failure analysis by comparing the defect occurrence situation of a workpiece, judged by said image signal processing unit, with failure analysis reference data and results of failure analysis by said data analysis processing unit are displayed on an input/output terminal.

According to an embodiment of the present invention, there is provided a foreign matter monitoring system as described above and characterized in that the control unit in said base system has a capability of preparing inspection recipes associated respectively with foreign matter monitors.

According to an aspect of the present invention, there is provided a process processing apparatus comprising: a platform which is evacuated and provided with a transport robot set up therein; plural process chambers each of which is placed around the platform and has a gate which is opened and closed for various processing when a workpiece is carried in or out through the gate by the transportation robot; a relay room which is connected to the platform and has a gate which is opened and closed; a cassette room in which plural cassette each accommodating plural workpieces are placed; and a small clean environment room which provides class 20 or better clean ambience for connection between the relay room and the cassette room and has a foreign matter monitoring optical head, the head including a detecting optical system for irradiating a workpiece with light and a detecting optical system for receiving reflected and scattered light from the workpiece and converting the received light to a detection image signal.

According to an aspect of the present invention, there is provided a process processing apparatus group comprising: plural process processing apparatuses each having a cassette room in which a cassette accommodating plural workpieces is placed, a process room to process workpieces carried in and out via a gate which is opened and closed, and a small clean environment room which has a transport robot carrying a workpiece between the cassette room and the process room and is kept clean at almost atmospheric pressure, wherein the plural process processing apparatuses are placed around the travel path of an automated guided vehicle; a foreign matter monitoring optical head containing a detecting optical system for irradiating a workpiece with light and a detecting optical system for receiving reflected and scattered light from the workpiece and converting the received light to a detection image signal is set up in each small clean environment room for a desired process processing apparatus; and an automated guided vehicle is used to transfer a cassette into and from the cassette room of each process processing apparatus.

According to an aspect of the present invention, there is provided an electronic transaction method (a method of electronic commerce), wherein the inspection equipment manufacturer which manufactures foreign matter monitors using a foreign matter monitoring system demands payment via a communication network to a chip device manufacturer for an economic effect by an increased yield which is brought about as a result of anti-failure countermeasures taken to an abnormal process processing apparatus located based on defect occurrence information acquired from the base system.

As mentioned above, according to the present invention, it is possible to realize a foreign matter monitoring system optimized for the whole of a manufacture line of semiconductors or the like, which can mount compact foreign matter monitors in clean ambience in main process processing apparatuses installed in the manufacture line and can use a base system to collectively process the digital image signals acquired from these many compact foreign matter monitors.

According to the present invention, it is also possible to realize a process processing apparatus in which a compact foreign matter monitor is set up optimally.

According to the present invention, it is possible to implement an electronic transaction method (a method of electronic commerce) using a foreign matter monitoring system.

While the invention has been described in its preferred embodiments, it is to be understood that the words which have been used are words of description rather than limitation and that changes within the purview of the appended claims may be made without departing from the true scope and spirit of the invention in its broader aspects.

BRIEF DESCRIPTION OF THE DRAWINGS

Other objects and advantages of the invention will become apparent from the following description of embodiments with reference to the accompanying drawings in which:

FIG. 18 is a diagram for explaining the contents of a database in a base system according to the present invention;

FIG. 19 is a diagram for explaining functions of a control unit in a base system according to the present invention;

FIG. 27 shows a screen which is displayed as a failure analysis result on an input/output terminal;

DETAILED DESCRIPTION OF THE PREFERRED EMBODIMENTS

Figure 1:
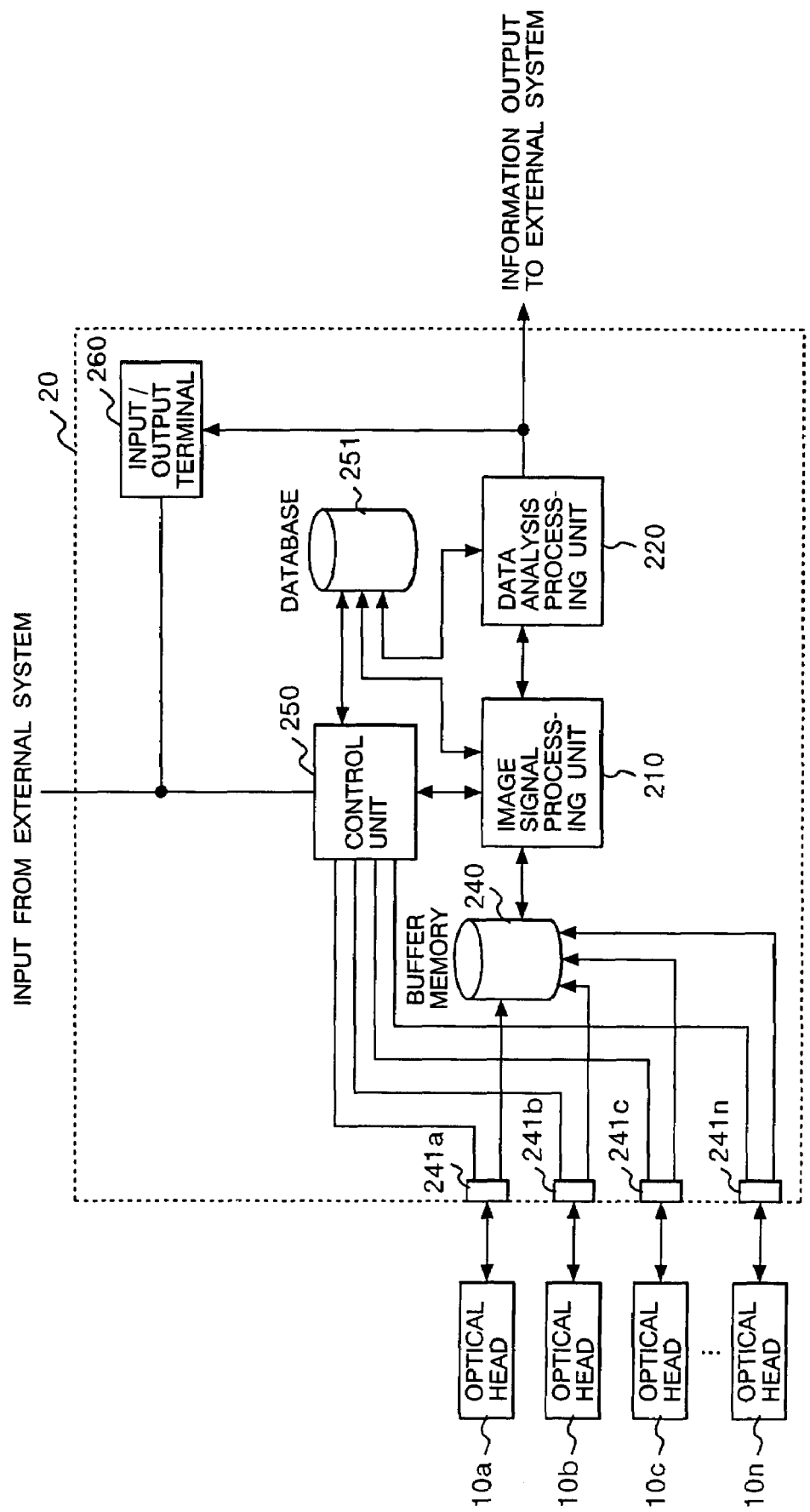
FIG. 1 shows the general configuration of an embodiment of a foreign matter monitoring system according to the present invention.

Referring to the drawings, the embodiments of the present invention will be described.

Figure 2:
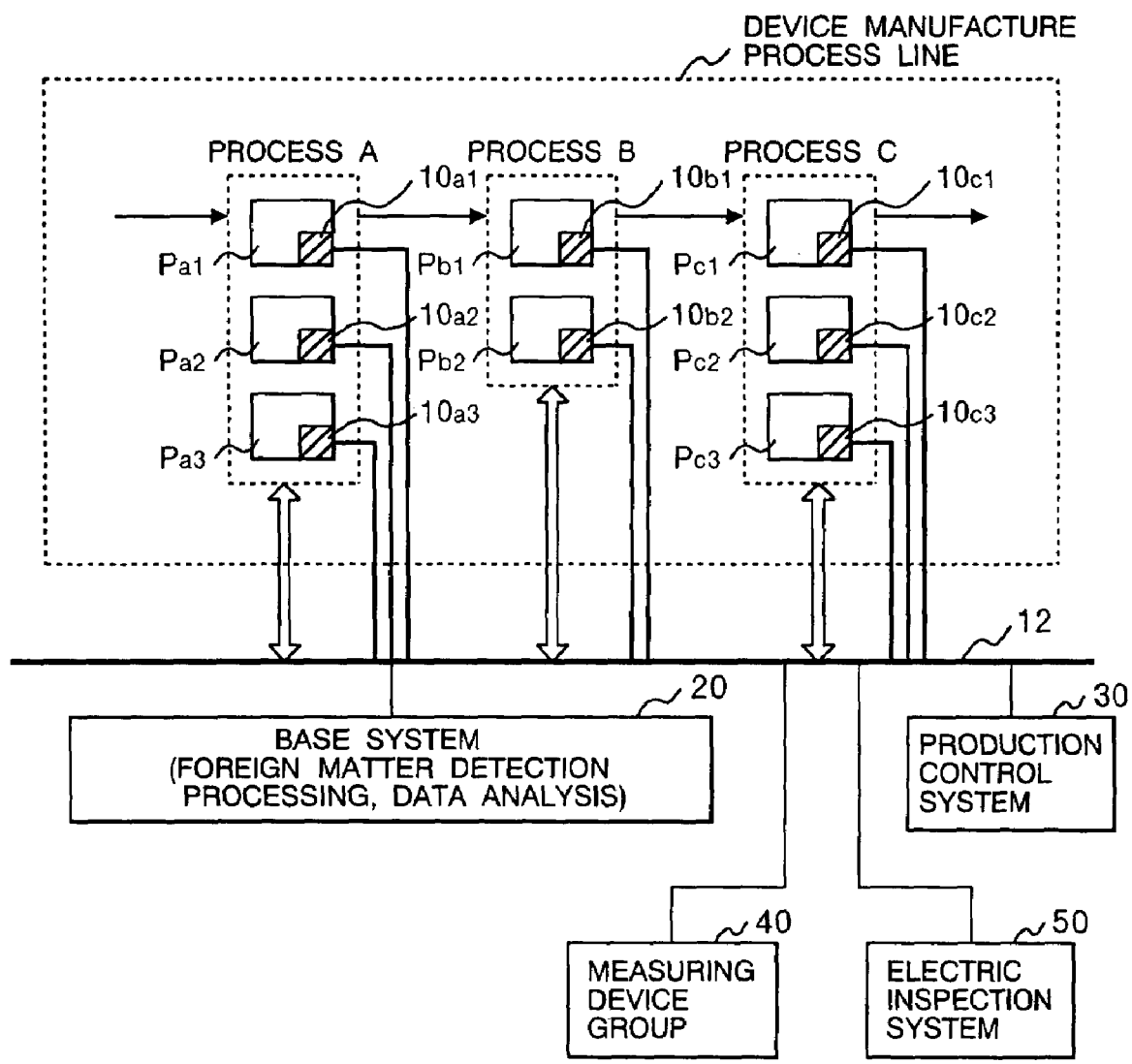
FIG. 2 shows an embodiment in which a foreign matter monitoring system according to the present invention is applied to a device manufacture process line.

An on-machine foreign matter monitor system according to the present invention intends to find dusting in any process of a semiconductor device manufacture line as early as possible so that the influence of the process dusting is limited to a minimum number of wafers without causing a mass of failures and, as shown in FIG. 1 and FIG. 2, includes compact foreign matter monitors (optical heads) 10a through 10n and a base system 20. Each compact foreign matter monitor 10, whose hardware configuration is minimized in order to save the cost price, is installed in one of process processing apparatuses (etching, sputtering, CVD, exposure and other processing apparatuses) Pa to Pm. The base system 20 has: reception ports 241a to 241n which at least receive A/D-converted digital image signals from the many compact foreign matter monitors 10a through 10n; an image signal processing unit 210 which receives monitor identification, inspection start and other signals and perform image signal processing in order to detect foreign matter (foreign particles) generated in any of the process processing apparatuses Pa through Pm placed in the manufacture line; and a data analysis processing unit 220 which, based on foreign matter detection signals obtained as the result of the image signal processing, performs data analysis processing in order to immediately judges whether and where abnormality has occurred and issue an instruction to stop the process processing apparatus P judged abnormal. The process processing apparatuses Pa through Pm where the compact foreign matter monitors 10a through 10m are respectively installed are the major one which are likely to generate foreign matter. In particular, a control unit 250 in the base system 20 is provided with an on/off monitor function in order to guarantee that a detection signal is incoming to the base system 20 from each compact foreign matter monitor 10 since detection processing and analysis processing are not done on the compact foreign matter monitor 10 side including the conveyance system arranged therein.

Then, how the above mentioned on-machine foreign matter monitor system is applied to a semiconductor device manufacture process line by using FIG. 2 will be described. Assume that the semiconductor device manufacture process line comprises a process A having process processing apparatuses Pa1 through Pa3 installed therein, a process B having process processing apparatuses Pb1 through Pb3 and a process C having process processing apparatuses Pc1 through Pc3. In each of these process processing apparatuses Pa1 through Pa3, Pb1 through Pb3 and Pc1 through Pc3, the compact foreign matter monitors (optical heads) 10a1 through 10a3, 10b1 through 10b3 and 10c1 through 10c3 are respectively mounted in clean ambience. The input and output of each of the many optical heads 10 in the respective processes A through C are connected to the base system 20 via, for example, a network 12. In addition, the process processing apparatuses P in the respective processes A through C are connected to a production management system (a production control system) 30 via, for example, the network 12 to perform production control. The base system 20, the production system 30, a measuring device group 40 having standalone type inspection devices (ordinary foreign matter inspection units, appearance inspection units, etc.) and an electric inspection system 50 which tests the operation of semiconductor circuits are connected to the network 12. Accordingly, the respective digital image signals given identification codes are regularly incoming to the base system 20 via the network 12 and reception ports 241a through 241c from the corresponding compact foreign matter monitors (each having an optical head) 10a1 through 10c3 installed in the process processing apparatuses Pa1 through Pc3 and are stored in a buffer memory 240. Each digital image signal can be read out therefrom by the image signal processing unit 210 by use of the corresponding identification code. The image signal processing unit 210 detects foreign matter signals by performing image processing consistently with a processing condition set to the compact foreign matter monitor. Based on the detected foreign matter signals, the data analysis processing unit 230 performs data analysis processing in order to create foreign matter distribution maps on an each wafer or lot basis, judge immediately whether the process processing apparatus is abnormal and, if so, issue an instruction to stop the apparatus.

Although FIG. 2 shows a continuous line having a sequence of manufacture processes, the monitor system may also be a line dispersed in a factory or process processing apparatuses of the same kind. Examples of a continuous line include an etcher, CVD, coater, developer, etc. In this case, the base system 20 can perform foreign matter control more finely so as to minimize the loss. If the monitor system is applied to a factory-wide manufacture line, the base system 20 can perform comprehensive foreign matter control. In addition, if the monitor system is applied to process processing apparatuses of the same kind, the base system 20 can control the foreign matter differences among the apparatuses and find an abnormal process processing apparatus.

Figure 3:
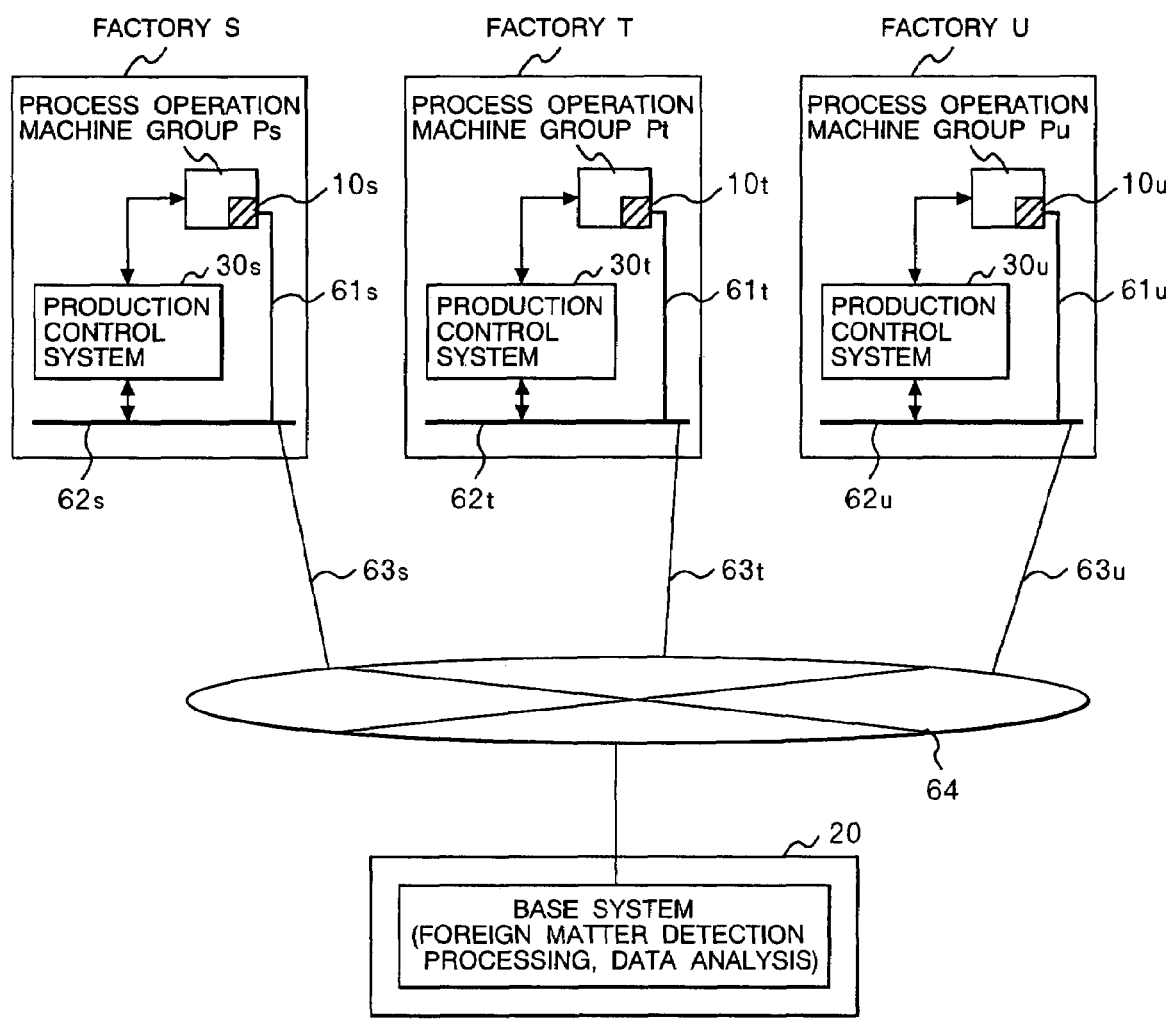
FIG. 3 shows an embodiment in which a foreign matter monitoring system according to the present invention is applied to among factories.

As shown in FIG. 3, the on-machine foreign matter monitor system can also be applied to among factories. Factories S, T and U respectively have process machine groups (process apparatus groups) Ps, Pt and Pu therein, each of which comprises a great number of process processing apparatuses. Compact foreign matter monitor groups 10s, 10t and 10u, mounted respectively in the machine groups, are connected to communication cable mains 62s, 62t and 62u in the respective factories via communication cables 61s, 61t and 61u. Production management systems (production control systems) 30s, 30t and 30u are respectively connected to the process processing apparatus groups (process operation machine groups) Ps, Pt and Pu via the communication cable mains 62s, 62t and 62u so as to provide management on an each factory basis. The communication cable mains 62s, 62t and 62u in the respective factories are connected to a communication network 64 such as the Internet via communication cables 63s, 63t and 64t. The communication network 60 is connected to a base system 20 located in, for example, an inspection equipment manufacturer. This allows the base system 20 to perform inter-factory foreign matter detection processing and data analysis to detect and stop abnormal process machines and therefore put foreign matter occurrence under inter-factory control. In addition, this allows the base system 20 to provide such information as foreign matter occurrence in a specific factory to that factory together with derived yield-related information.

Then, embodiments of a compact foreign matter monitor (having an optical head) 10 including a conveyance system will be described. Each embodiment described below is mounted on a main process machine (a main process apparatus), a part of a manufacture line constituting an on-machine foreign matter monitor system according to the present invention.

Figure 4:
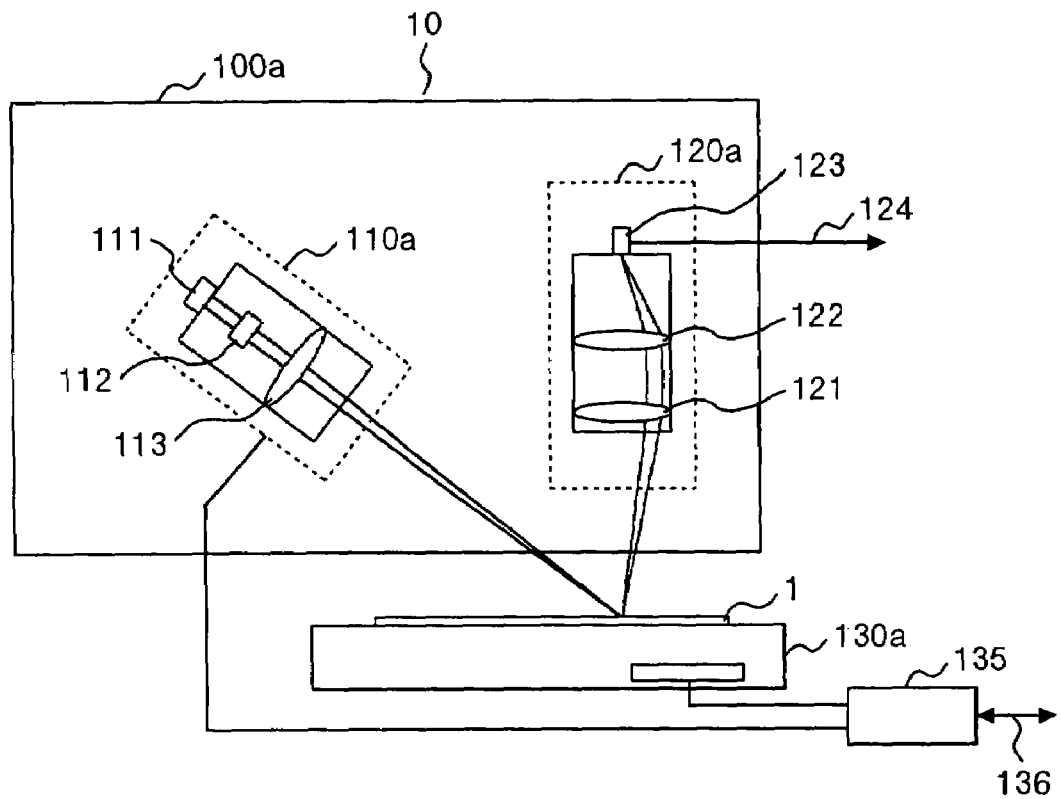
FIG. 4 is a front view of a first embodiment of a compact foreign matter monitor set up in each process operation machine (each process processing apparatus) according to the present invention.

As shown in FIG. 4, a first embodiment of a compact foreign matter monitor 10 includes an optical unit (optical head) 100a, a locating system 130a and a control device 135. The optical unit 100a comprises an illuminating optical system 110a and a detecting optical system 120a. The illuminating optical system 110a comprises: an illumination light source 111 consisting of a laser light source, etc.; an AO (Acousto-Optical) deflector 112 which deflects the illumination light emitted from the illumination light source 111; and a condenser lens 113 which condenses the deflected light from the AO deflector 112 to irradiate a wafer 1 at a large incident angle. The detecting optical system 120a comprises: an objective lens 121 to condense scattered, reflected light from the wafer 1; a focusing lens 122 to focus the condensed reflected light from the objective lens 121; and an optical detector 123 which receives an optical image formed by the focusing lens 122, converts it to an image signal, A/D-converts the signal and outputs the resulting digital image signal 124. The locating system 130a carries the wafer 1 mounted thereon. The control device 135 controls the locating system 130a, the AO deflector 112, starts and stops inspection and controls the intensity of illumination from the illumination light source 111 as necessary. The structure of the compact foreign matter monitor, including the control circuit, is simplified this manner so as to lower the cost price.

Figure 5:
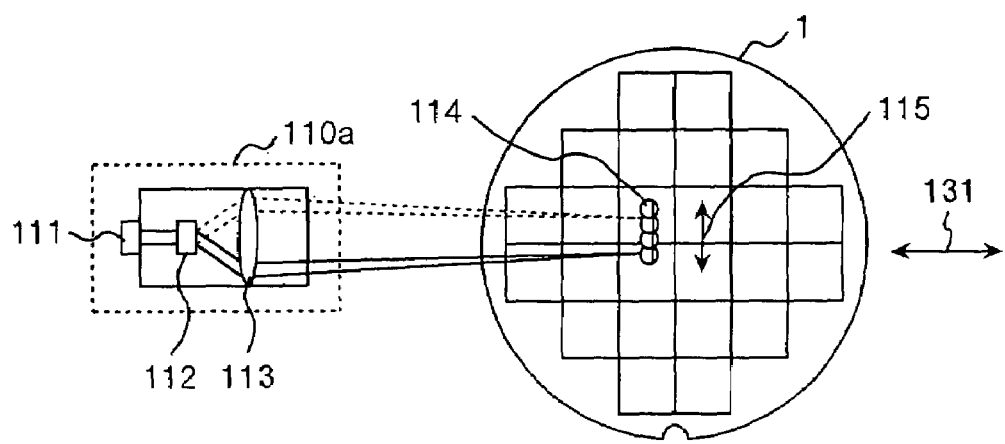
FIG. 5 is a top view of the embodiment shown in FIG. 4.

In the first embodiment, as shown in FIG. 5, an illumination spot 114 condensed through the condenser lens 113 is deflected by the AO deflector 112 to scan the wafer 1 in the scanning direction 115 of the illumination light while the wafer 1 is moved in the wafer conveyance direction 131 by the locating system 130a so that a specified area is scanned two-dimensionally. As a result, a digital image signal 124 obtained from the specified area is given the identification code of the compact foreign matter monitor and output for transmission to a reception port of the base system. This scanned area can be specified by the process processing apparatus. In addition, in the case of the first embodiment, the locating system 130a has only to move in the wafer conveyance direction 131. For example, it is possible to use a wafer transport robot carrying the wafer 1 between a loader or unloader (wafer cassette) and a process room as described later. That is, the first embodiment can be configured in such a manner that foreign matter detection is done while the wafer 1 is on a hand of the wafer transport robot. From each compact foreign matter monitor 10 to the base system 20, at least a detection start signal is entered with its identification code via the reception port 241. In short, this is the minimum control information which must be transferred (exchanged) between the control unit 250 in the base system 20 and the control device 135 in the compact foreign matter monitor.

Figure 6:
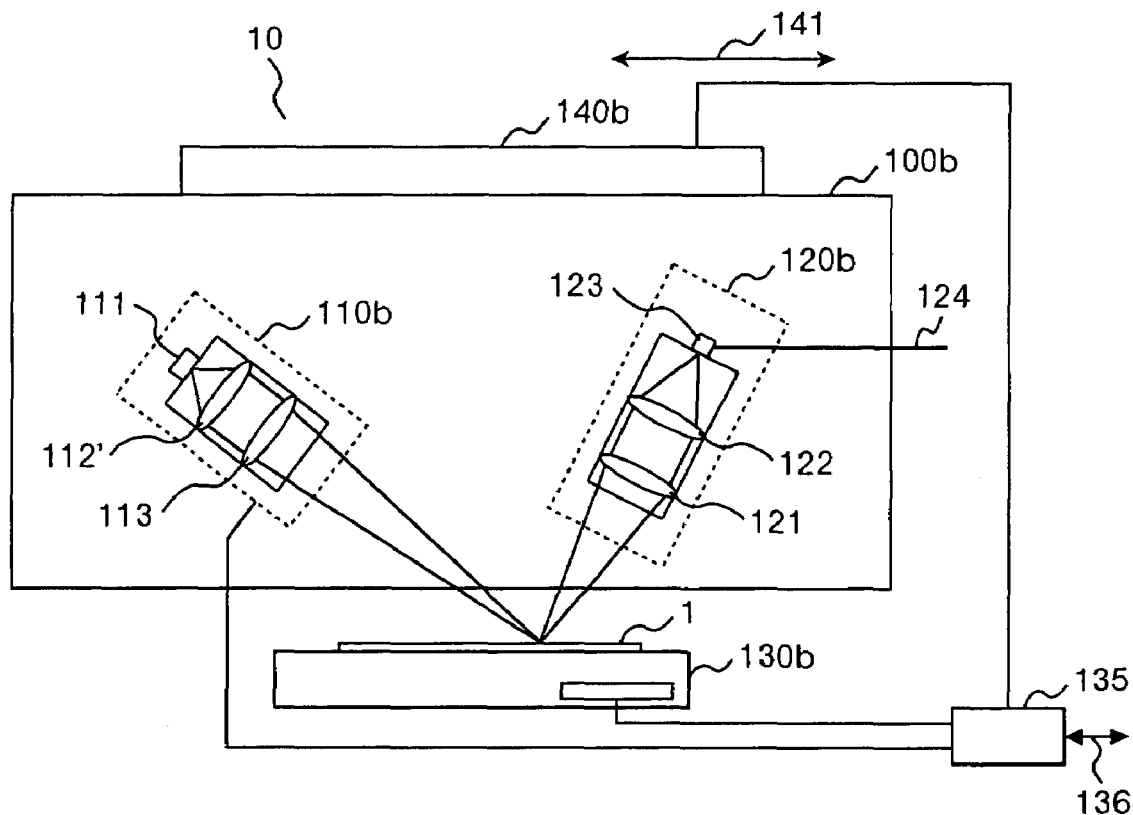
FIG. 6 is a front view of a second embodiment of a compact foreign matter monitor set up in each process processing apparatus according to the present invention.
Figure 7:
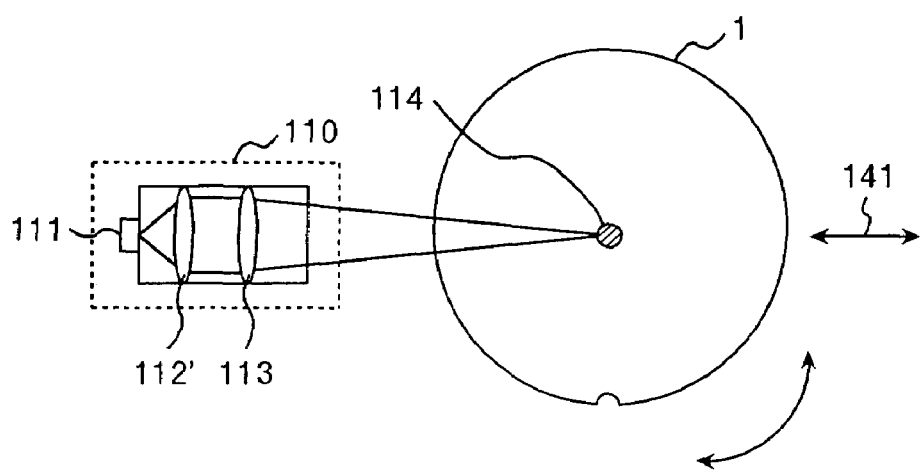
FIG. 7 is a top view of the embodiment shown in FIG. 6.

A second embodiment of the compact foreign matter monitor 10, as shown in FIG. 6, is applicable for foreign matter detection where pre-alignment is done with a rotary stage. Since a pre-alignment optical system (not shown) exists where pre-alignment is done, either an optical unit (optical head) 100b must be arranged so as not to interfere with the pre-alignment optical system or the pre-alignment optical system and optical unit (optical head) 100b must be able to advance and retreat (movable) so as not to interfere with each other. Accordingly, the second embodiment has a mechanism for advancing and retreating the optical unit 100b (an optical unit locating system 140b for positioning in the optical unit movement direction 141). A locating system 130b has a rotary wafer mount stage which rotates for pre-alignment with the orientation flat. In the case of the second embodiment, the optical unit (optical head) 100b is configured in the same manner as the first embodiment except that the illuminating optical system 110b can use a condenser lens 112" instead of an AO deflector. In addition, in order to prevent interference with the pre-alignment optical system (not shown), the optical axis of the detecting optical system 120b is deviated from the perpendicular direction to such a degree that the regularly reflected light does not go incident on the iris of the objective lens 121. Accordingly, in the second embodiment, a pre-specified area on the wafer is scanned in a spiral or arc fashion by an illumination spot 114 as shown in FIG. 7. As a result, a digital image signal 124 obtained from the specified area is output from the optical detector 123. From each compact foreign matter monitor 10 to the base system 20, at least a detection start signal is entered with its identification code via a reception port 241. In short, this is the minimum control information which must be transferred (exchanged) between the control unit 250 in the base system 20 and the control device 135 in the compact foreign matter monitor.

Figure 8:
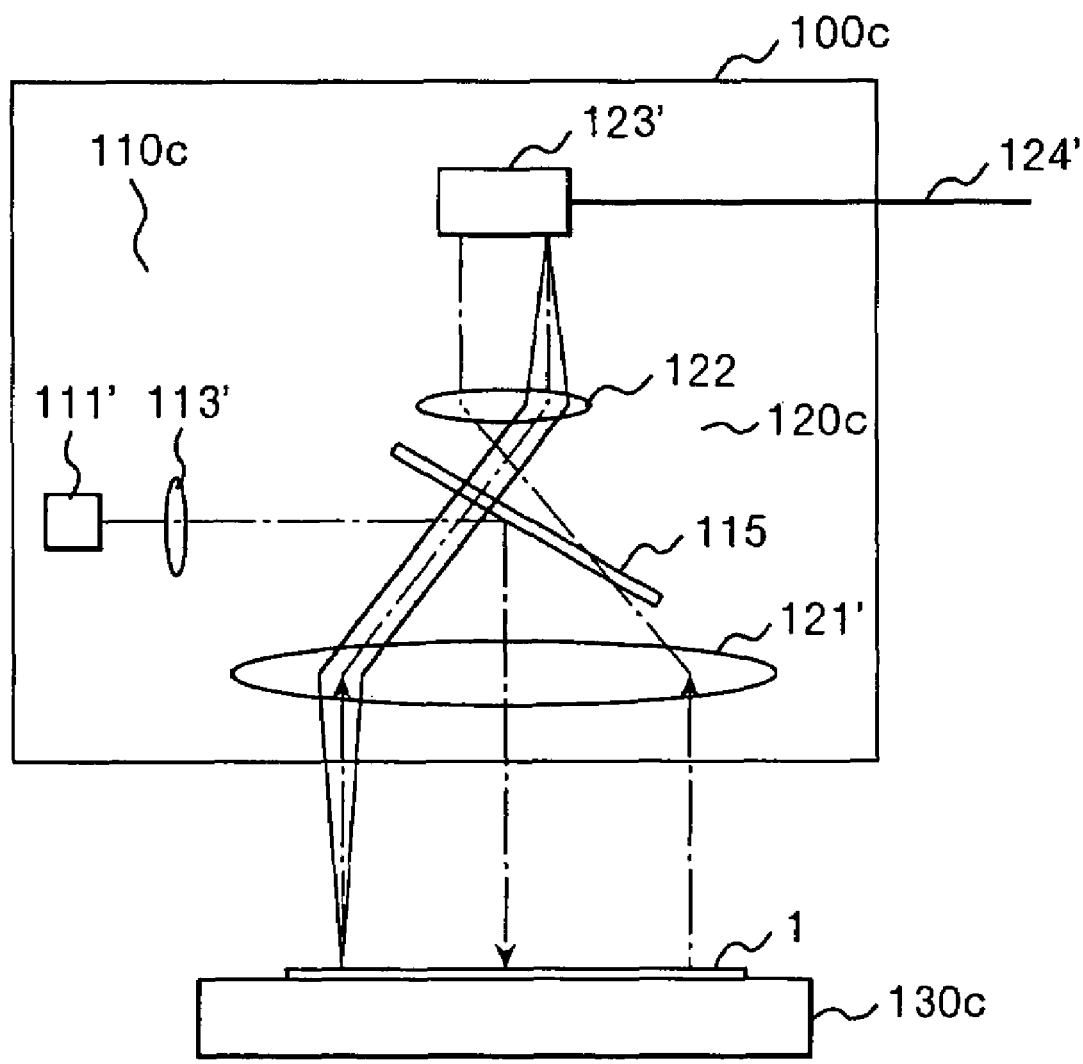
FIG. 8 is a front view of a third embodiment of a compact foreign matter monitor set up in each process processing apparatus according to the present invention.
Figure 9A:
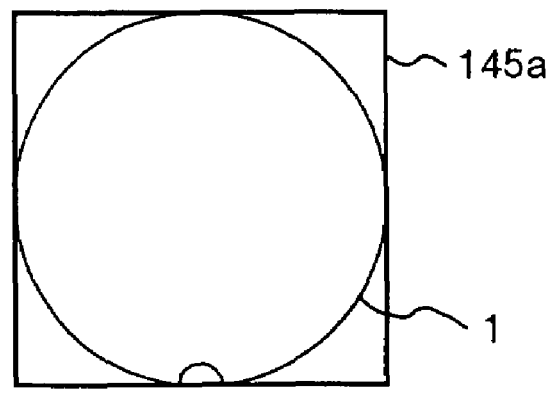
FIG. 9a shows a case in which the whole surface of a wafer is inspected at a time by a compact foreign matter monitor and FIG. 9b shows a case in which a wafer is partially inspected with a reduced pixel size.
Figure 9B:
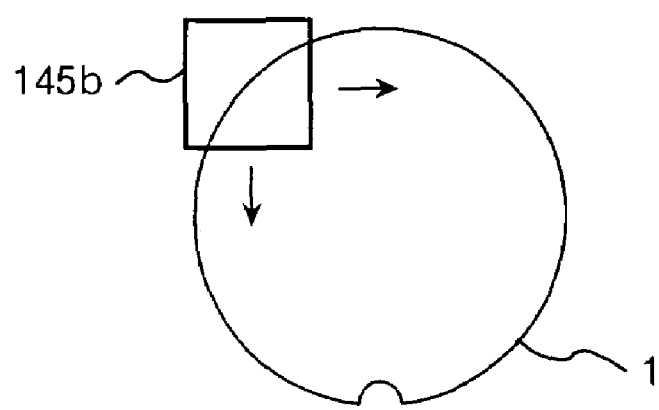

A third embodiment of the compact foreign matter monitor 10 assumes that almost the whole surface of a wafer 1 mounted on a stationary stage 130c having no conveyance system is inspected at a time as shown in FIG. 8. The third embodiment has an optical unit (optical unit) 100c comprising an illuminating optical system 110c and a detecting optical system 120c. The illuminating optical system 110c comprises an illumination light source 111', a magnifying optical system 113' by which the luminous flux from the illumination light source 111' is magnified so as to irradiate the whole surface of a wafer and a half mirror 115 by which the magnified luminous flux from the magnifying optical system 113' is reflected so as to irradiate the whole surface of the wafer. The detecting optical system 120c comprises a telecentric optical system 121' and 122' and a TV camera (detector) 123' having an A/D conversion circuit. Accordingly, in the third embodiment, a digital image signal 124' covering the whole surface of the wafer is obtained by the TV camera 123', with the signal 124' having a field of view 145a as shown in FIG. 9a. To decrease the pixel size of the TV camera (detector) 123', i.e., raise the detection sensitivity, it is necessary to partially move the detector or telecentric optical system so that the field of view 145b for pickup is narrowed as shown in FIG. 9b.

Figure 10A:
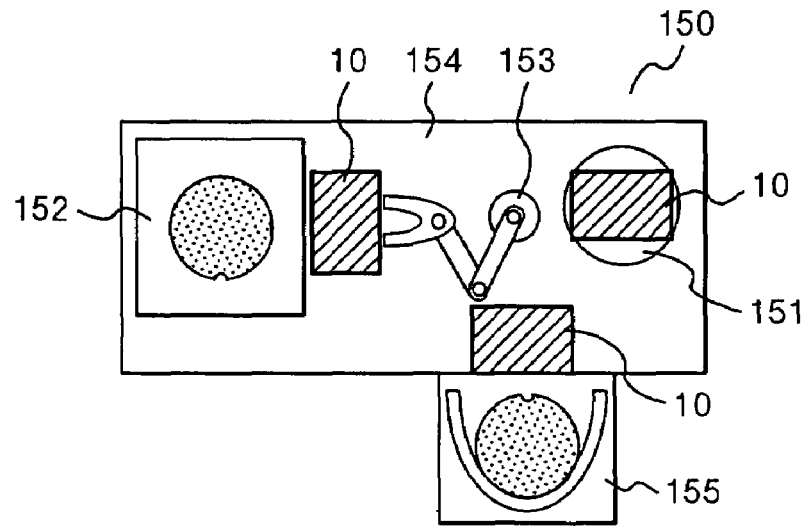
FIGS. 10a and 10b show top and front views of a batch processing type process processing apparatus in which compact foreign matter monitors according to the present invention is set up, respectively.
Figure 10B:
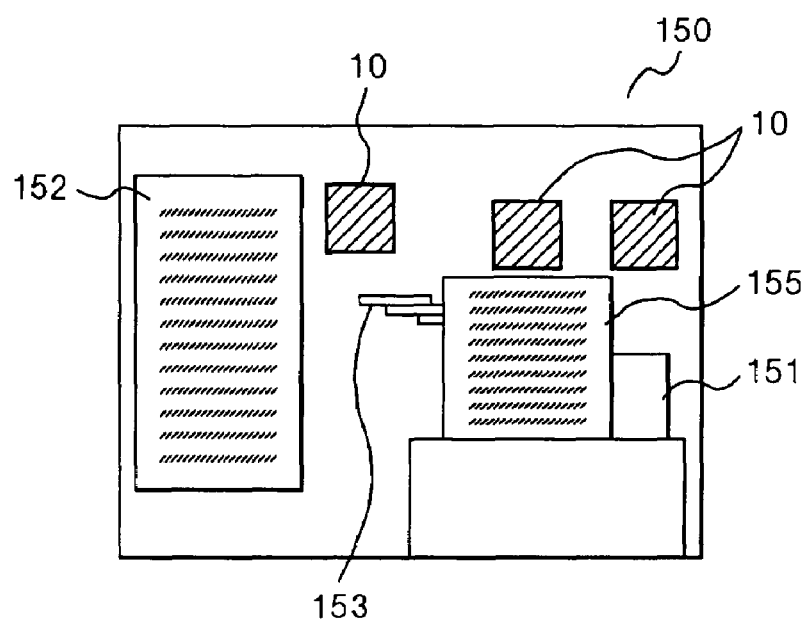

Then, how compact foreign matter monitors 10 are installed in a variety of process processing apparatuses will be described with reference to drawings. FIGS. 10a and 10b show a part of a batch processing type process processing apparatus (for LP-CVD (Low Pressure Chemical Vapor Deposition), etc.) in which a compact foreign matter monitor 10 is installed. A batch processing type process processing apparatus 150 comprises a cassette room 155, a preliminary treatment area 151, a batch type process room 152 and a wafer transport robot 153. Wafers 1 are accommodated in cassettes which are sealed to prevent penetration of foreign matter when they are carried into and out from the cassette room 155 which exists in clean ambience. To and from the cassette room 155, the preliminary treatment area 151 and the batch type process room 152, the wafer transport robot 153 conveys wafers 1 through a platform 154. Since the platform 154 is kept clean to class 20 or better, the possibility of foreign matter sticking to wafers is low. When a wafer is transferred between a cassette and the platform 154, the front gate of the cassette is opened and closed or it is opened and closed after an elevator along which the wafer is moved between the container and a slot is lifted down. Therefore, foreign matter may stick to wafers only in the batch type process 152. Accordingly, the compact foreign matter monitor 10 may be set up in an area where wafers are transferred by the wafer transport robot 153 to and from the platform 154, in an area before the gate of the batch type process room 152 or in the preliminary treatment area 151. A locating system 130a to locate the compact foreign matter monitor 10 can be implemented by using the action of the arm of the robot 153. If the preliminary treatment area 151 has a rotary stage, it may be used, too.

Figure 11:
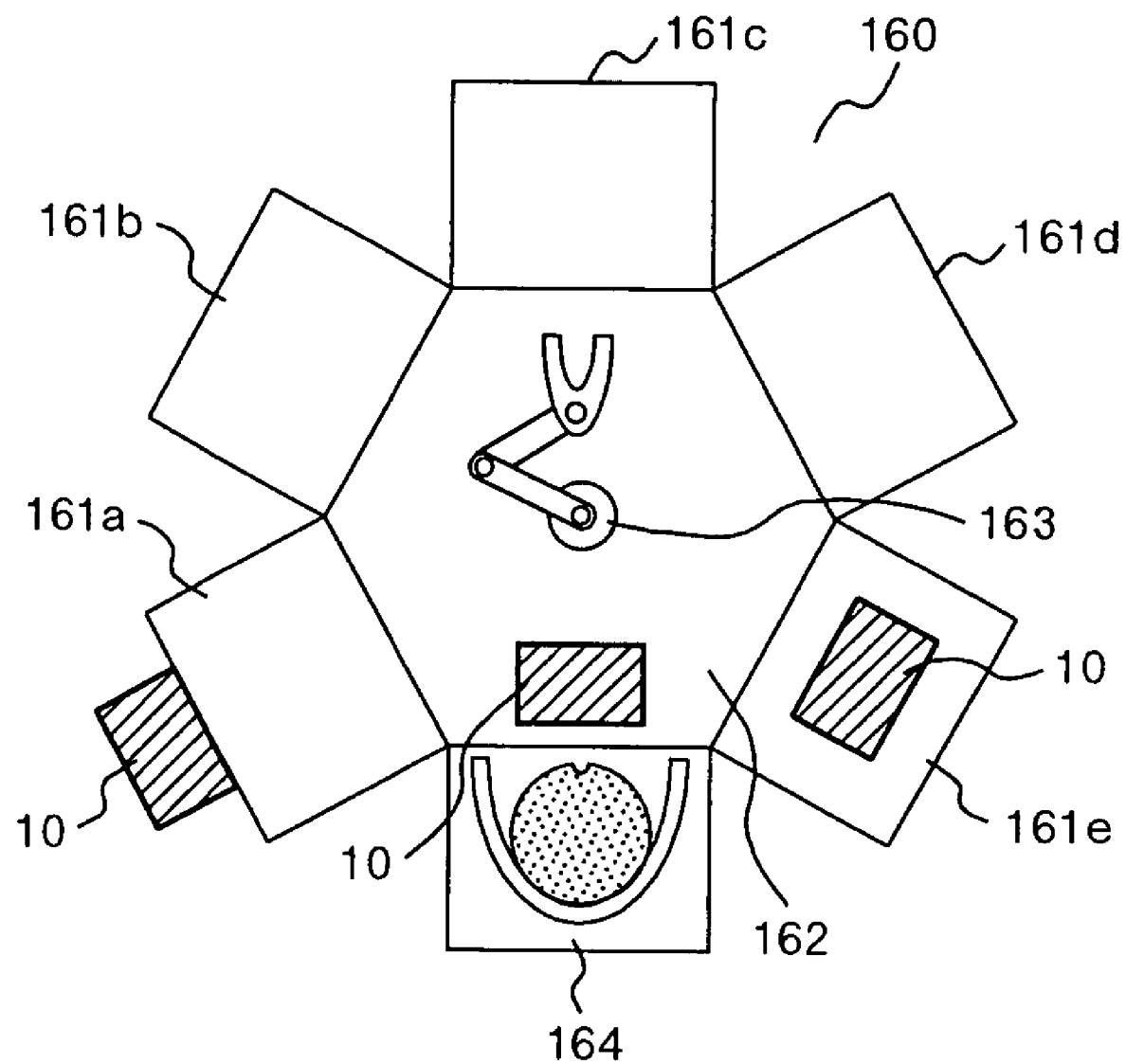
FIG. 11 shows a plan view of a single-wafer multi-chamber type process processing apparatus (1) in which compact foreign matter monitors according to the present invention is set up.

FIG. 11 shows a part of a single-wafer multi-chamber type process processing apparatus (for P-CVD, dry etching, sputtering, etc.) where a compact foreign matter monitor 10 is installed. This process processing apparatus 160 has a cassette room 164, five process chambers 161a through 161e and a platform 162 provided with a wafer transport robot 163. Similar to the above-mentioned one 155, the cassette room 164 exists in clean ambience and stores a cassette accommodating a wafer. If the cassette is 8 inches in size, it is called an standard mechanical interface. If the cassette is equal to or larger than 12 inches, it is called a front opening unified pod.

The compact foreign matter monitor 10 may be set up in an area where wafers are transferred by the wafer transport robot 163 to and from the platform 162, in a process chamber 161c and around an process chamber 161a. If the compact foreign matter monitor 10 is set up around the process chamber 161a, it is assumed that the side wall of the process chamber 161a has a transparent window (not shown) through which a wafer therein can be observed by the compact foreign matter monitor 10.

Figure 12:
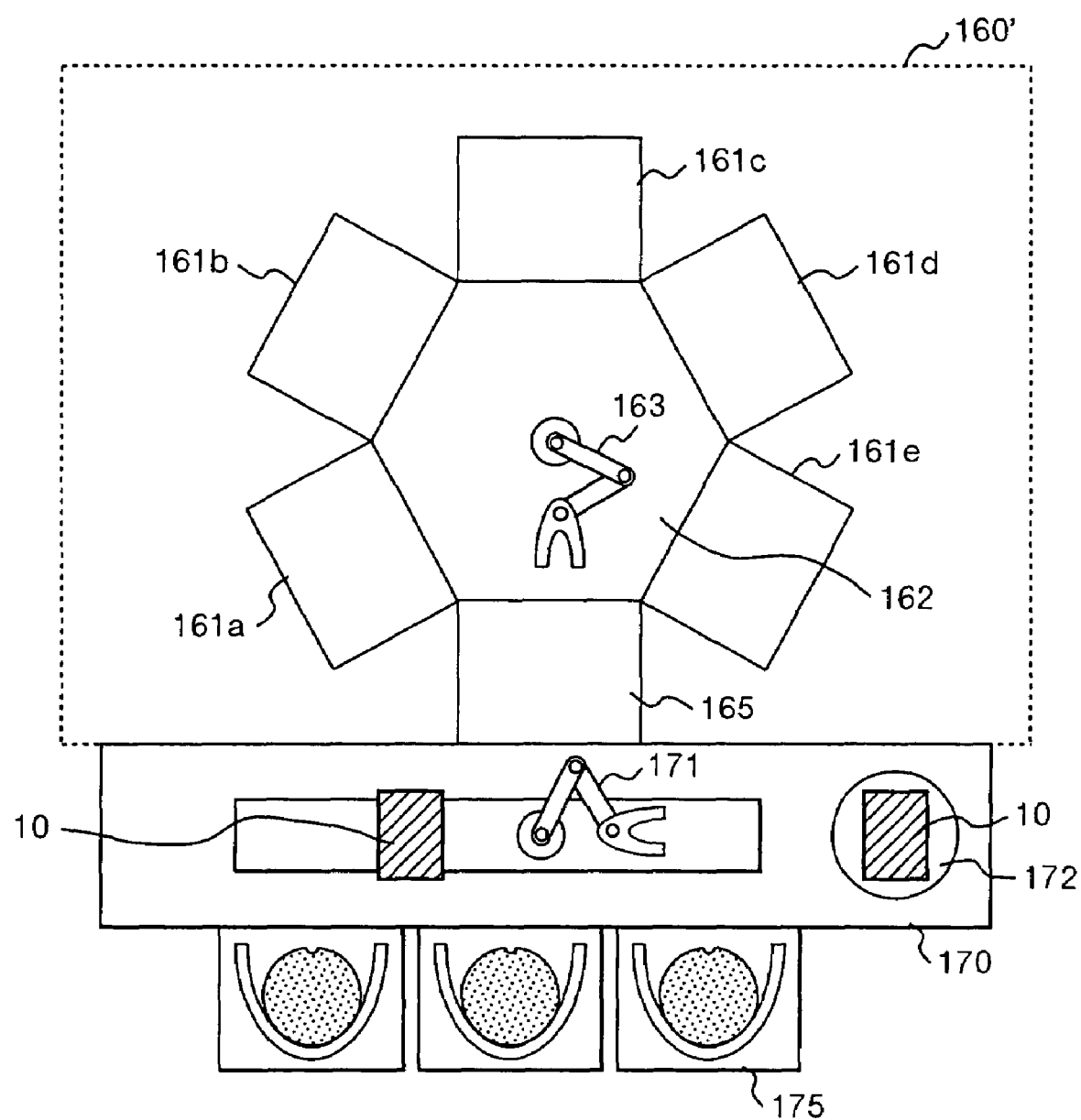
FIG. 12 shows a plan view of a process processing apparatus in which compact foreign matter monitors according to the present invention are set up in a small clean environment room which is connected to a platform.

In FIG. 12, compact foreign matter monitors 10 are set up in a small clean environment connected to the wafer platform of a process processing apparatus. This small clean environment room 170 has a wafer transport robot 171 which passes wafers between the wafer relay room 165 of the process processing apparatus 160' and each of plural ports 175 where cassettes are placed. In addition, the small clean environment room 170 has a pre-alignment section 172. Ambience in the small clean environment room 170 is kept clean to class 20 or better (substantially class 1) at around the atmospheric pressure. Needless to say, each of the plural ports 175 is a place into which a gate-closed hermetic cassette accommodating a wafer in its clean environment is carried from external. The wafer transport robot 171 takes out a wafer into the clean mini environment 170 from a gate-opened cassette placed in a desired one of the plural ports 175 which are kept clean to class 20 or better. Then, the wafer transport robot 171 carries the wafer to the pre-alignment section 172 and mounts the wafer on its rotary stage. In the pre-alignment section 172, the wafer's orientation flat is optically detected and the rotary stage is rotated so as to direct the orientation flat to a certain direction. With this, pre-alignment is complete with the orientation flat of the wafer mounted in the pre-alignment section 172. Then, the wafer transport robot 171 lifts up the pre-aligned wafer and mounts it on a stage in the wafer relay room 165. This wafer mounted on the stage in the wafer relay room 165 is brought into the respective process chambers 161a through 161e sequentially by a wafer transport robot 163 installed in a platform 162. After processing is complete, the wafer is mounted on the stage in the wafer relay room 165. Then, the wafer transport robot 171 in the small clean environment room 170 takes out the wafer from the stage in the wafer relay room 165, puts it in the relevant cassette and closes its gate, making it possible to carry out the sealed cassette into the external ambience (kept clean to class 1000 to 10000 at atmospheric pressure).

As described above, if the small clean environment room 170 is included, the compact foreign matter monitor 10 may be set up in the rotary stage-used pre-alignment area 172 or within the operation range of the arm of the wafer transport robot 171 in the small clean environment room 170

Figure 13:
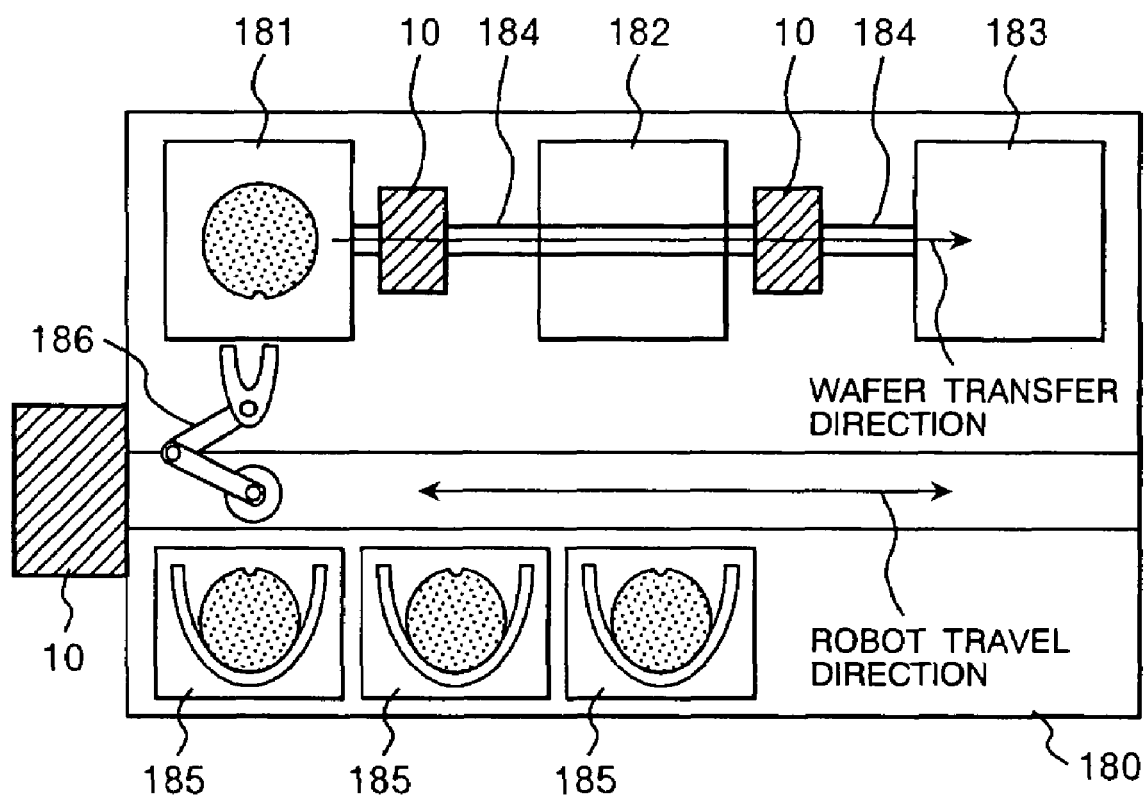
FIG. 13 shows a plan view of a single-wafer continuous type process processing apparatus in which compact foreign matter monitors according to the present invention are set up.

FIG. 13 shows a part of a single-wafer continuous type process processing apparatus (for atmospheric pressure CVD, washing, resist coating, etc.) where the compact foreign matter monitor 10 is set up. The process processing apparatus 180 comprises: a process room 181 having a resist coater; a process room 182 having an exposure system; a process room 183 having a development unit; a wafer transport belt 184 to convey a wafer among these process rooms; and a wafer transport robot 186 which takes out a wafer from a desired cassette room 185 into the process room 181 and carries the wafer processed in the process room 183 into a desired cassette room 185. Since the inside of the process processing apparatus 180 is kept clean to class 20 or better (substantially 1) similar to the above-mentioned small clean environment room 170, foreign matter occurs mainly in the process rooms 181 through 183. Therefore, the compact foreign matter monitor 10 is set up for between process rooms or a travel end of the wafer transport robot 186 where ambience is kept clean to class 20 or better at around atmospheric pressure.

Figure 14:
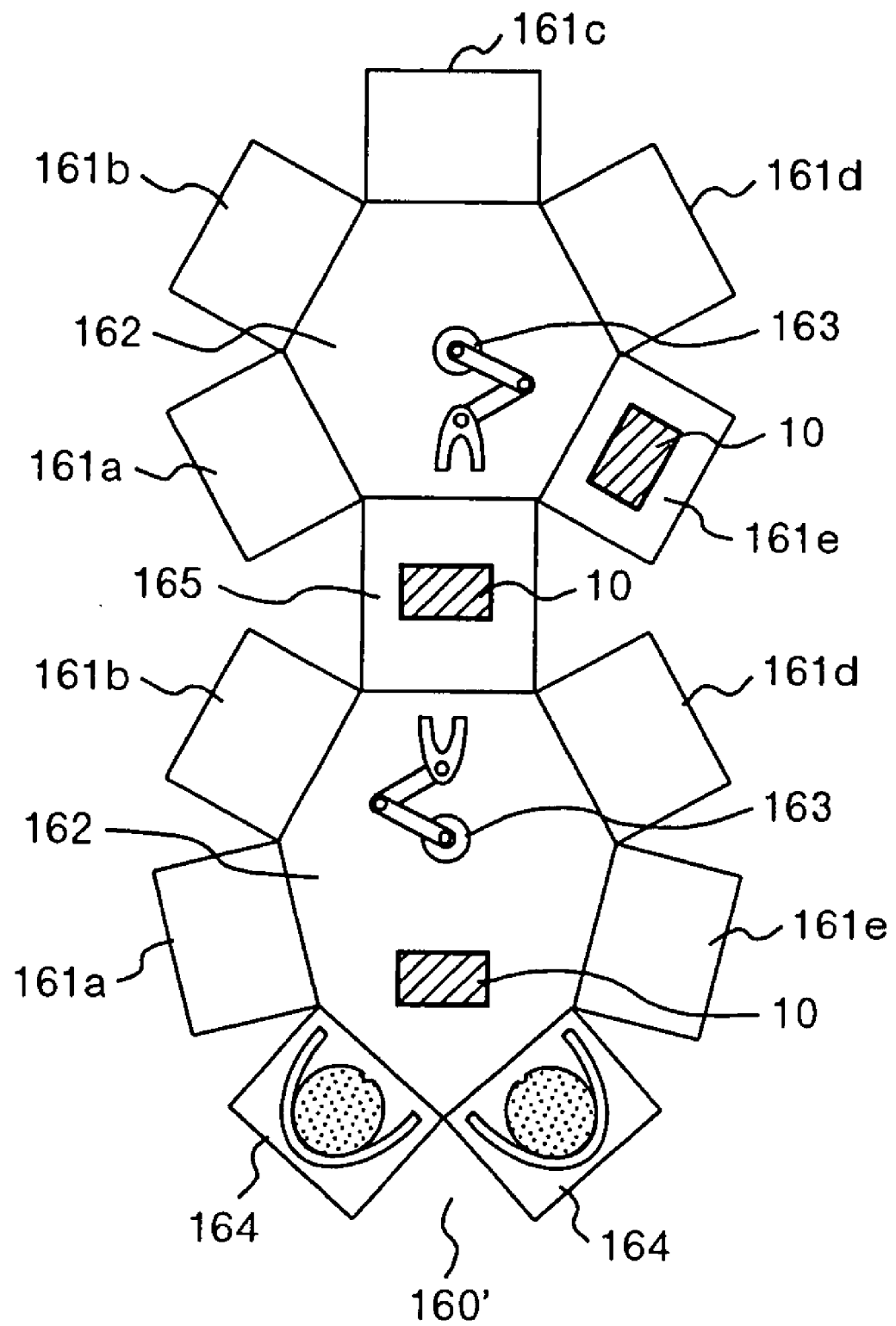
FIG. 14 shows a top view of a single-wafer multi-chamber type process processing apparatus (2) in which compact foreign matter monitors according to the present invention is set up.

FIG. 14 shows a part of a single-wafer multi-chamber type process processing apparatus (for P-CVD, dry etching, sputtering, etc.) where a compact foreign matter monitor 10 is set up. This process processing apparatus 160' has a relay room 165 between multi-chamber sets and one multi-chamber set is provided with a plurality of cassette rooms 164. The compact foreign matter monitor 10 is set up in the platform 162 of one multi-chamber set, in the relay room 165, where ambience is kept clean to class 20 or better, or in one process chamber 161e belonging to the other multi-chamber set.

Figure 15:
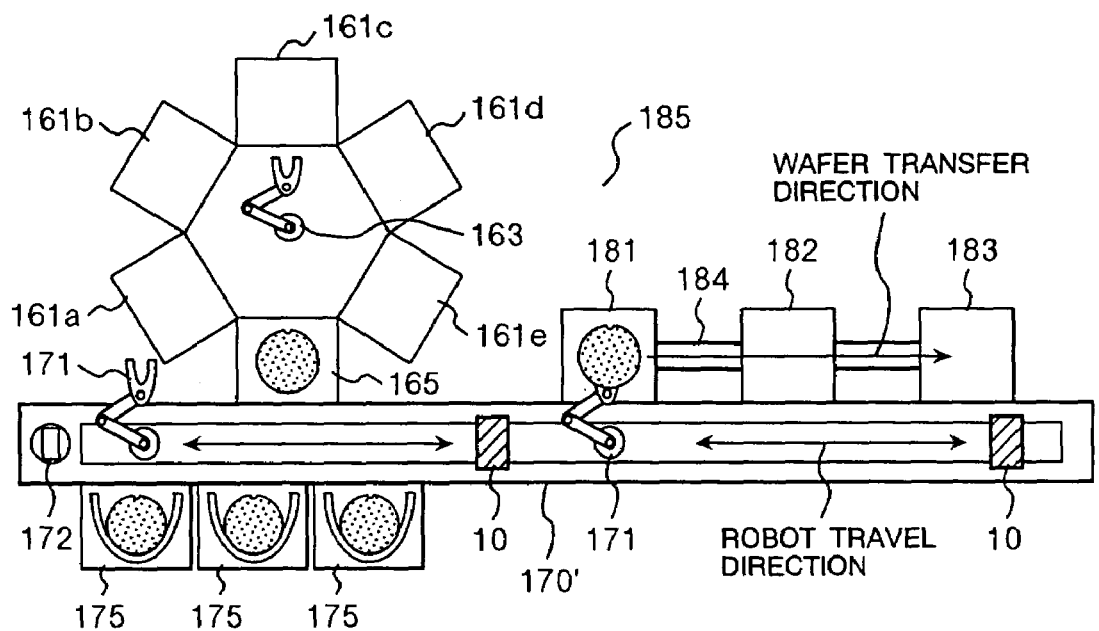
FIG. 15 shows a process processing apparatus in which compact foreign matter monitors according to the present invention are set up in a small clean environment room which is larger than that of FIG. 12.

FIG. 15 shows where a compact foreign matter monitor 10 is set up in a process processing apparatus having a small clean environment room which is equivalent to but longer than the one shown in FIG. 12. This process processing apparatus 185 has the long clean mini environment 170' kept clean to class 20 or better and further includes process rooms 181 through 184 (those shown in FIG. 13) placed along the mini environment 170'. A plurality of wafer transport robots 171 are provided in the clean mini environment 170'. The compact foreign matter monitor 10 is set up in such a position as to be accessible by some wafer transport robot 171 (or automated guided vehicle) in the clean mini environment 170'.

Figure 16:
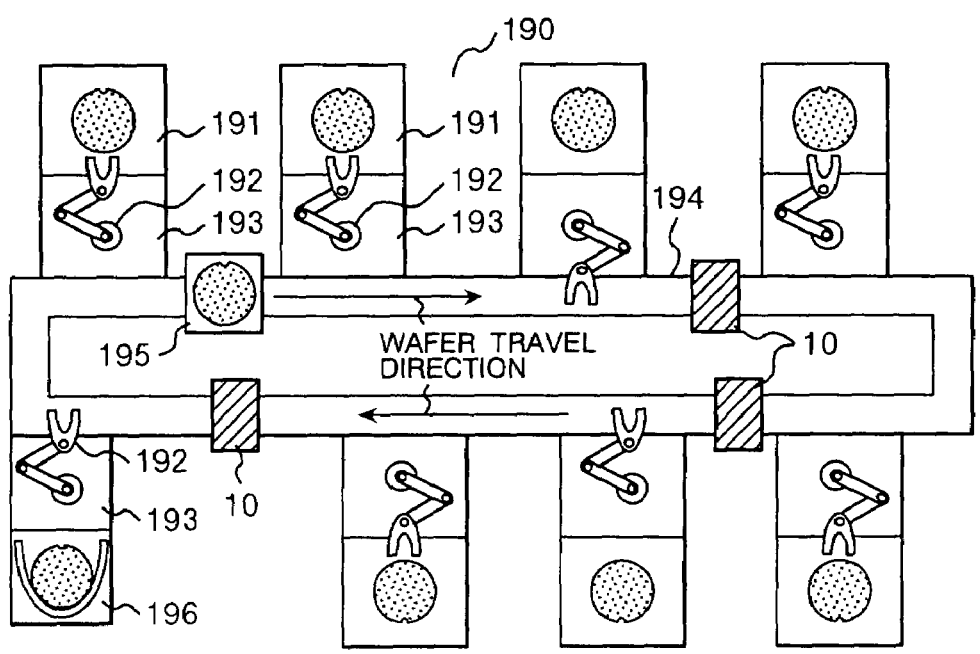
FIG. 16 shows a process processing apparatus in which compact foreign matter monitors according to the present invention are set up in a small clean environment room which is still larger than that of FIG. 15.

FIG. 16 shows where a compact foreign matter monitor is set up in a process processing apparatus which has small clean environment room and process chamber pairs placed along the travel path of a wafer stage. This process processing apparatus 190 comprises a plurality of equipment sets, each of which includes a process chamber 191 and a small clean environment room 193, placed along the travel path 194 of the wafer stage 195 and a wafer transfer robot 192 which transfers a wafer between a cassette port 196 at an end of the machine and the travel path 194. Cassettes are also transferred between the cassette port 196 and a cassette transport system (not shown) including a bay-to-bay automated guide vehicle, etc. The compact foreign matter monitor 10 is to be set up over the travel path 194 along which the wafer stage 195 moves. Not only the platforms 193 provided with the wafer transfer robot 192 but also the travel path 194 are kept clean to class 20 or better by air curtain or the like.

Figure 17:
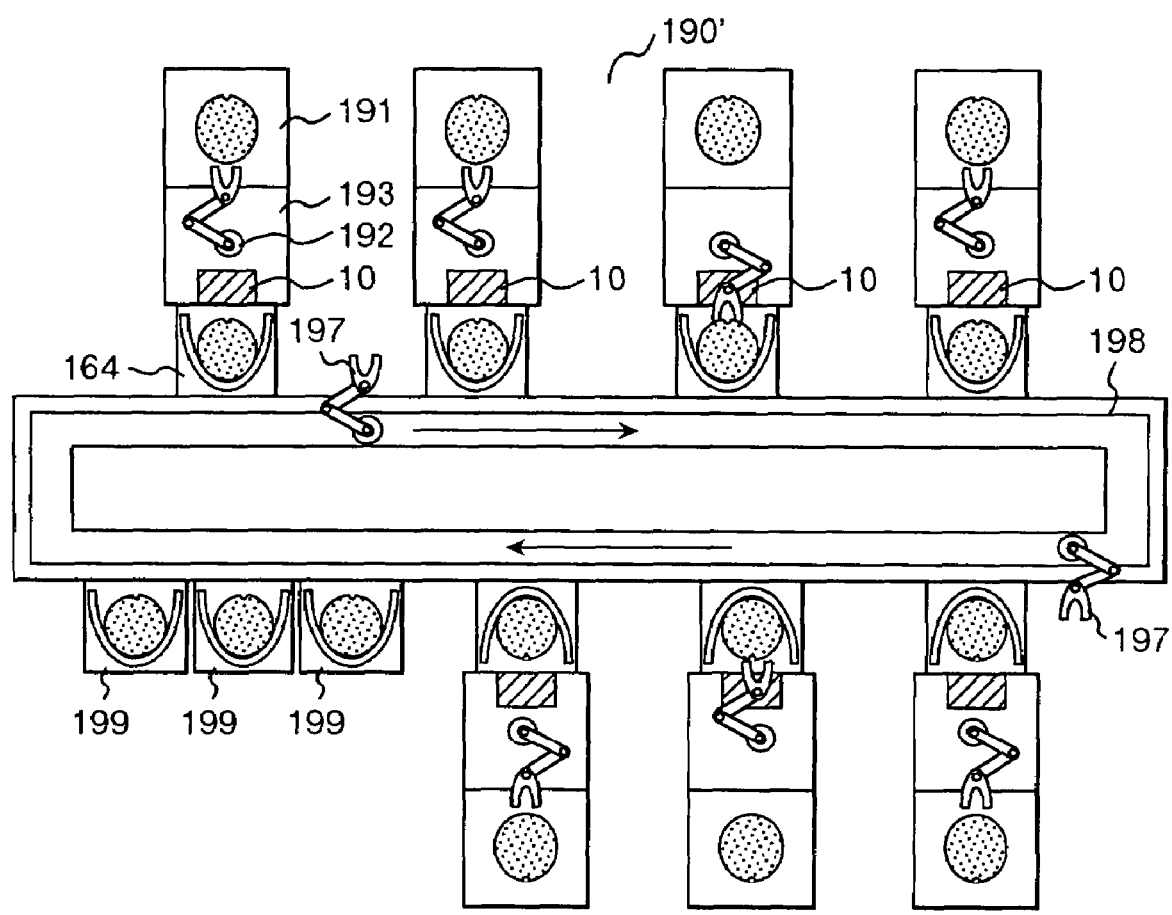
FIG. 17 shows a plan view of a system comprising many process processing apparatuses according to the present invention, each of which has a process chamber, a clean small environment room as a platform with a compact foreign matter monitor set up therein, and a cassette room and is placed along the transport route of an automated guided vehicle (AGV)

FIG. 17 shows where a compact foreign matter monitor is set up in a process processing apparatus which has small clean environment room, process chamber and cassette room sets placed along the travel path of an automated guided vehicle. This process processing apparatus 190' comprises a plurality of equipment sets, each of which includes a process chamber 191, a small clean environment room 193 and a cassette room 164, placed along the travel path 198 of the automated guided vehicle 197, and cassette ports 199 at an end of the machine. In each small clean environment room 193, a wafer transport robot 192 to transfer a wafer and a compact foreign matter monitor 10 are set up. All small clean environment rooms 193 and cassette rooms 164 which are connected to the respective process chambers 191 are kept clean to class 20 or better at atmospheric pressure. The automated guided vehicle 197 transfers sealed cassettes between the cassette rooms 164 and the cassette ports which are kept clean to class 1000 to 10000.

It is preferable to add a small clean environment room 170, 193, which is kept clean to class 20 or better, to a process processing apparatus and set up a compact foreign matter monitor 10 in the small clean environment rooms 170, 193 as described above.

Then, embodiments of the base system 20 shown in FIG. 1 through FIG. 3 will be described. As shown in FIG. 1, image data (digital image signals) 124a through 124n from compact foreign matter monitors 10a through 10n enter the base system 20 via its reception ports 241a through 241n and are stored together with the identification codes of the compact foreign matter monitors 10a through 10n in their associated addresses in the buffer memory 240. In addition, inspection start signals and the like from each of the compact foreign matter monitors 10a through 10n enter the base system 20 via its reception ports 241a through 241n and are stored in the control unit 250. Needless to say, the control unit 250 may store identification codes and other various information, which are obtained from the compact foreign matter monitors 10a through 10n, into the database 251. Identification codes may be given to either the compact foreign matter monitor side or the reception port side.

Although using "identification codes" is assumed in the above description as a method for identifying each of the many data originators, that is, the compact foreign matter monitors 10a through 10n, identification is also possible by assigning a different communication data frequency to each compact foreign matter monitor (broadband communication). Such broadband communication allows high speed data transmission by using an existing network. In addition, data from a plurality of compact foreign matter monitors can be transmitted using one line of the network.

Figure 22:
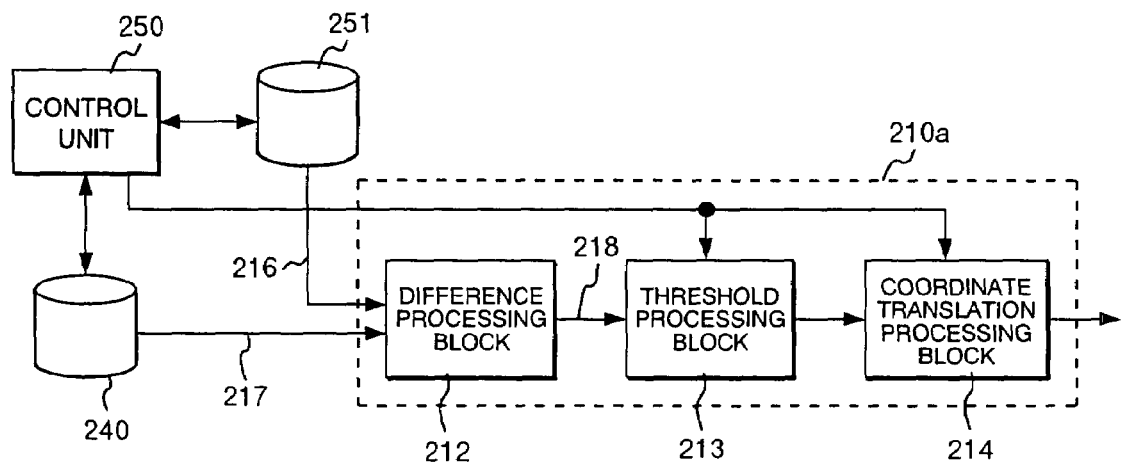
FIG. 22 is a diagram for explaining the general configuration of a first embodiment of an image signal processing unit in a base system according to the present invention.

In addition, wafer flow information, such as the type of the product (wafer) being processed by the process processing apparatus P in which the compact foreign matter monitor is set up and the name of the process (including the lot number), and manufacture line information, such as the name of the process processing apparatus (including the location of the compact foreign matter monitor), the name of the manufacturer of the process processing apparatus and the name of the factory ((a) wafer process data, (b) wafer layout data, (c) data on the process processing apparatus and compact foreign matter monitor as listed in FIG. 18) are received by the control unit 250 from an external system such as a production management system 30 and stored in the database 251. Also in the database 251, history data ((h) failure analysis reference data (foreign matter distribution data)) obtained for each compact foreign matter monitor as a result of analysis by the data analysis unit 230 are stored in association with the above-mentioned corresponding wafer flow information (manufacture process information) and manufacture line information. In addition, if the image signal processing unit 210a is configured as shown in FIG. 22, (d) inspection reference image data (reference digital image signal), which is to be compared with the image data retrieved from the buffer memory 240, is prepared and stored in the database 251. Alternatively, image data obtained from a foreign matter-free wafer by a compact foreign matter monitor can also be used as (d) inspection reference image data (reference digital image signal).

In summary, as listed in FIG. 18, (a) wafer process data, (b) in-wafer layout data, (c) data on the process processing apparatus and compact foreign matter monitor, (d) inspection reference image data, (e) inspection recipe data ((e-1) threshold for judgment, (e-2) quantity of illumination light, (e-3) inspection area, (e-4) inspection method), (f) inspection result data, (g) defective area image data and (h) failure analysis reference image data are stored in the database 251. In particular, of the inspection recipe data, (e-3) inspection area and (e-4) inspection method (relative positional coordinates of the optical head relative to the wafer by XY scan or rotary scan) are used for coordinate translation from each foreign matter detection signal to the wafer being inspected.

In addition, the control unit 250 has the control functions listed in FIG. 19 (①) compact foreign matter monitor on/off check function, ② signal processing timing control function, ③ inspection recipe prepare function, ④ identification code recognize function, ⑤ inspection recipe select function, ⑥ alarm output function and ⑦ compact foreign matter monitor optical head maintenance management function, etc.).

Figure 20:
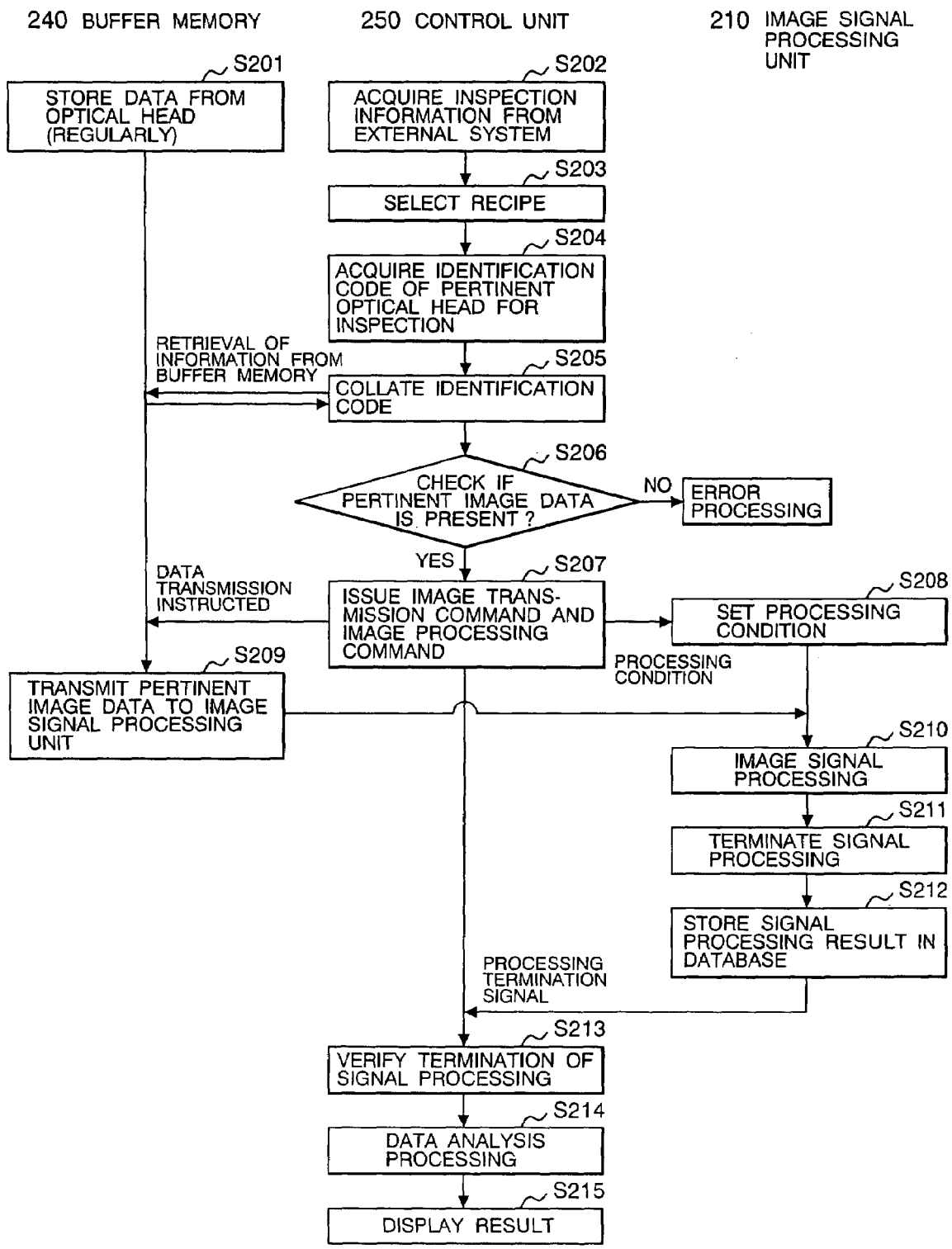
FIG. 20 shows flows of processing done in a base system designed in such a manner that operation of a control unit is triggered by data from an external system according to the present invention.

Then, flows of processing which is triggered by data from an external system (a compact foreign matter monitor as the case may be) will be described with reference to FIG. 20. In the flows of processing in the base system 20 shown in FIG. 20, the control unit 250 performs control so as to immediately start inspection processing as described below if inspection information is received from an external system. The buffer memory 240 is always storing digital image data from the compact foreign matter monitors 10a through 10n (S201). The control unit 250 obtains inspection information (process data, layout data, requirement data on the process processing apparatus and compact foreign matter monitor for inspection, etc.) from an external system such as the production management system 30 and stores them in the database 251 (S202). Then, based on the obtained inspection information, the control unit 250 selects an inspection recipe (reference image data for comparison, threshold for judgment, inspection area, quantity of illumination light, inspection method, etc.) (S203). Then, the control unit 250 obtains the identification code of an optical head for which the inspection recipe is selected (S204) and, based on the obtained identification code, searches the buffer memory 240 for the corresponding information (S205). If no corresponding image data is found in Step 205, the control unit 250 performs error processing (Step 206). Otherwise, the control unit 250 issues an image transmission command and image processing command (S207). This error processing includes in AND OR some of the following: (I) waiting for a certain period of time and then retrying retrieval with the identification code, (II) indicating on the input/output terminal 260 that image data is absent, (III) logging the inspection processing error (product type and process) and (IV) terminating the inspection processing without doing anything. Then, the control unit 250 sets an image signal processing condition based on the selected recipe (S208) and the buffer memory 240 transmits the relevant image data to the image signal processing unit 210 based on the image transmission command (S209). The image signal processing unit 210 processes the received image data according to the set image signal processing condition (S210) and, upon completion (S211), stores the signal processing result ((f) inspection result data and (g) defective area image data) in the database 251 (S212). After verifying that the signal processing is terminated (S214), the control unit 250 not only instructs the data analysis unit 220 to perform data analysis processing (S214) and outputs the result to, for example, the input/output terminal 260 for display thereon but also outputs analysis information and alarm information to external systems such as the production management system 30 and process processing apparatus P as necessary.

Figure 21:
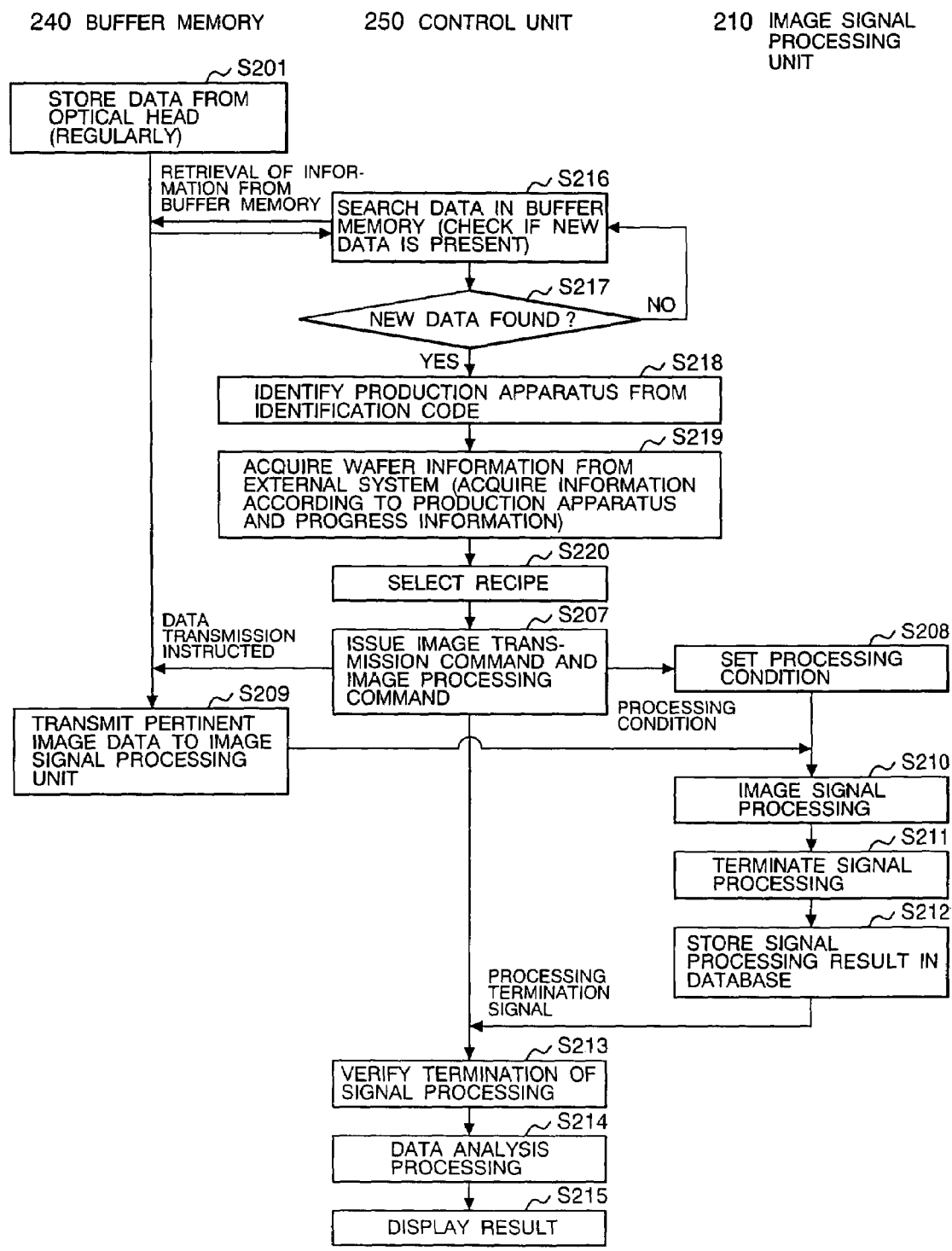
FIG. 21 shows flows of processing done in a base system in which a control unit is designed to access an external system according to the present invention.

Then, with reference to FIG. 21, flows of processing done in the base system 20 where the control unit 20 is designed to access external systems will be described. In the flows of processing shown in FIG. 21, the control unit 250 controls an external system to search for inspection information when image data is stored in the buffer memory 240. Of the flows of processing, steps S216 through S220 are different from those in FIG. 20. In these steps, the control unit 250 firstly searches the buffer memory (S216) to check if new image data is stored (S217) and, if present, identifies the corresponding process processing apparatus from the identification code (S218). The control unit 250 obtains wafer information and other inspection information from external systems such as the production management system 30 according to the identified process processing apparatus (S219) and, based on the obtained inspection information, selects an inspection recipe (S220). The subsequent flows of processing are same as those shown in FIG. 20.

The control unit 250 can automatically prepare inspection recipes. Based on the mechanical data (quantity of illumination light, illumination angle and angle of the detecting optical axis) obtained from the respective compact foreign matter monitors 10 with wafer type-based reference image data (raw digital image signals), the control unit 250 automatically prepares inspection recipes where inspection areas, judgment thresholds and others are specified. Judgment thresholds can also be determined by a method described in Japanese Patent Laid-Open No. 2000-105203.

Then, embodiments of the image signal processing unit 210 will be described with reference to FIG. 22, FIG. 23 and FIG. 24. Since the image signal processing unit 210 must process great amounts of detected image data which are obtained from many compact foreign matter monitors 10a through 10n and stored in the buffer memory 240, high speed processing is required. The image signal processing unit 210 may also be designed in such a manner that priority is given to process processing apparatuses which has a possibility of suffering a great amount of foreign matter when detection image data is incoming from many compact foreign matter monitors 10a through 10n.

In the case of an embodiment shown in FIG. 22, the image signal processing unit 210a comprises a difference processing block 212, a threshold processing block 213 and a coordinate translation processing block 214. As shown in FIG. 24, the difference processing block 212 obtains a difference between reference image data 216 stored in the database 251 and detection image data 217 obtained from each compact foreign matter monitor by using a synchronization signal 219 and outputs the difference data 218. In the threshold processing block 213, the difference data 218 output from the difference processing block 212 is binarized to a foreign matter signal according to a judgment threshold specified in an inspection recipe which is selected from the database 251 according to the wafer type, quantity of illumination light, etc. In the coordinate translation block 214, the coordinates of the foreign matter signal detected by the threshold processing block 213 are translated into those in the coordinate system of the wafer under inspection according to the inspection area and inspection method specified in the inspection recipe selected from the database 251. The synchronization signal 219 is given to both data 216 and 217 which enter the difference processing block 212 so that the difference between the reference image data 216 and detection image data 217 can be calculated. A coordinate of each detected foreign matter can be determined according to the number of pixels from the synchronization signal 219. As for the inspection area and inspection method, the relative positional relation between the optical head and wafer in each process processing apparatus must be measured and stored in the database 251 in advance as inspection recipe data. Needless to say, the difference processing block 212 may perform difference processing for an inspection area specified in the selected inspection recipe data. In this manner, the coordinate translation block 214 of the image signal processing unit 210a provides foreign matter occurrence maps 231a through 231n for the respective wafers under inspection by the compact foreign matter monitors 10a through 10n.

Figure 23:
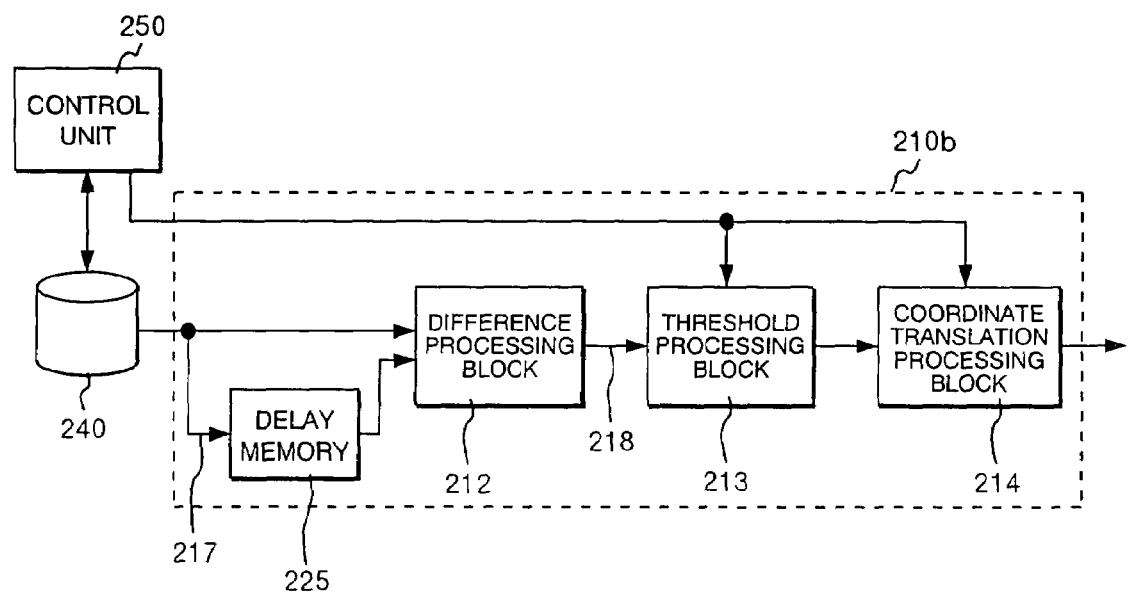
FIG. 23 is a diagram for explaining the general configuration of a second embodiment of an image signal processing unit in a base system according to the present invention.
Figure 24:
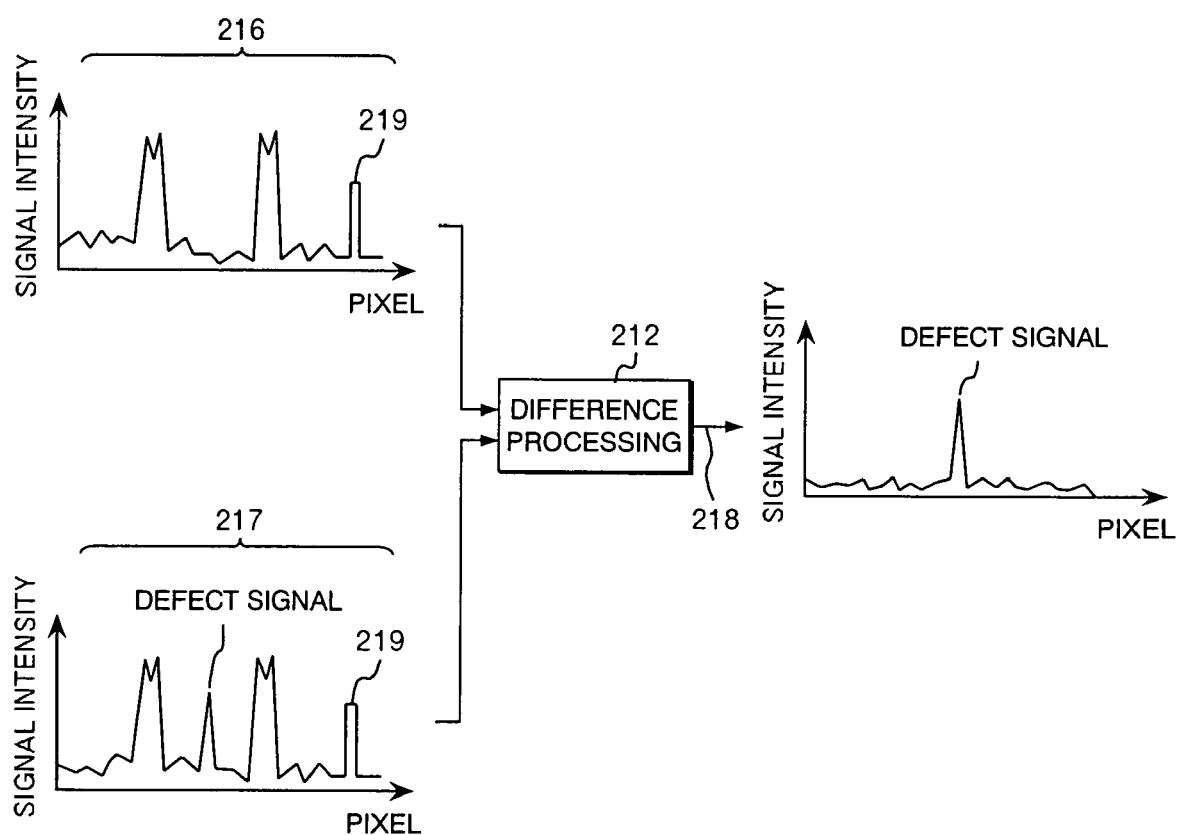
FIG. 24 is a diagram for explaining image processing in an image signal processing unit.

In the case of an embodiment shown in FIG. 23, the image signal processing unit 210b comprises: a delay memory 225 in which detection image data 217 from each of the compact foreign matter monitors 10a through 10n is delayed by one repetitive pattern (one chip); a difference processing block 212; a threshold processing block 213; and a coordinate translation block 214. This embodiment is different from that shown in FIG. 22 in that the reference image data (reference digital image signal) is obtained from the delay memory 225.

Figure 25:
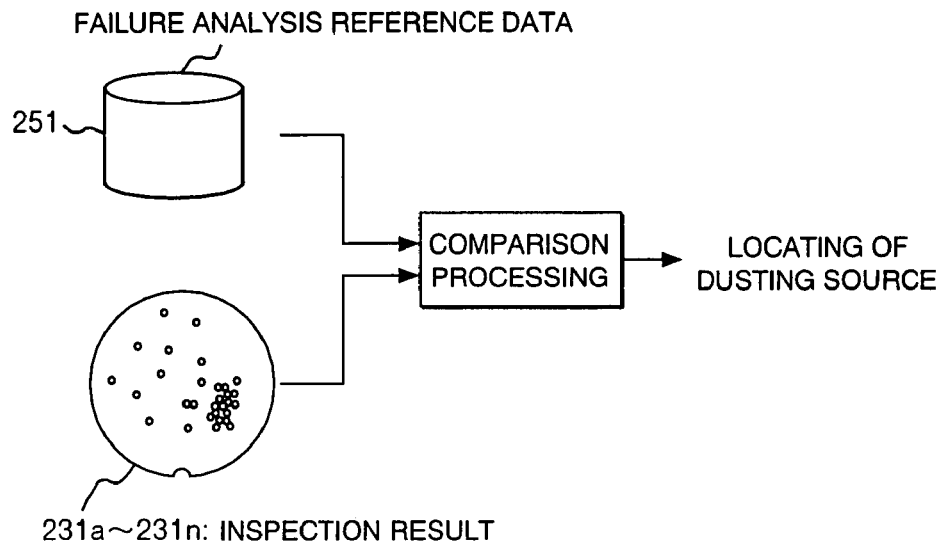
FIG. 25 is a diagram for explaining how a probable dusting source is located by a data analysis processing unit in a base system according to the present invention.

Then the data analysis processing unit 220 concretely will be described. In the data analysis processing unit 220, as shown in FIG. 25, foreign matter and other defect inspection results 231a through 231n, which are obtained from the image signal processing unit 210 in association with the respective compact foreign matter monitors 10a through 10n, are compared with foreign matter distribution data (sampled past inspection results) which are failure analysis reference data stored in the database 251. Then, the data analysis processing unit 220 analyzes the results of comparison to locate probable dusting sources among the process processing apparatuses Pa through Pn. If a result of comparison is abnormal, an alarm is not only displayed with a probable dusting source on the input/output terminal 260 but also sent to the external production management system 30 and the process processing apparatus judged abnormal. The notified process processing apparatus immediately stops its process operation so as not to generate defective wafers.

Figure 26:
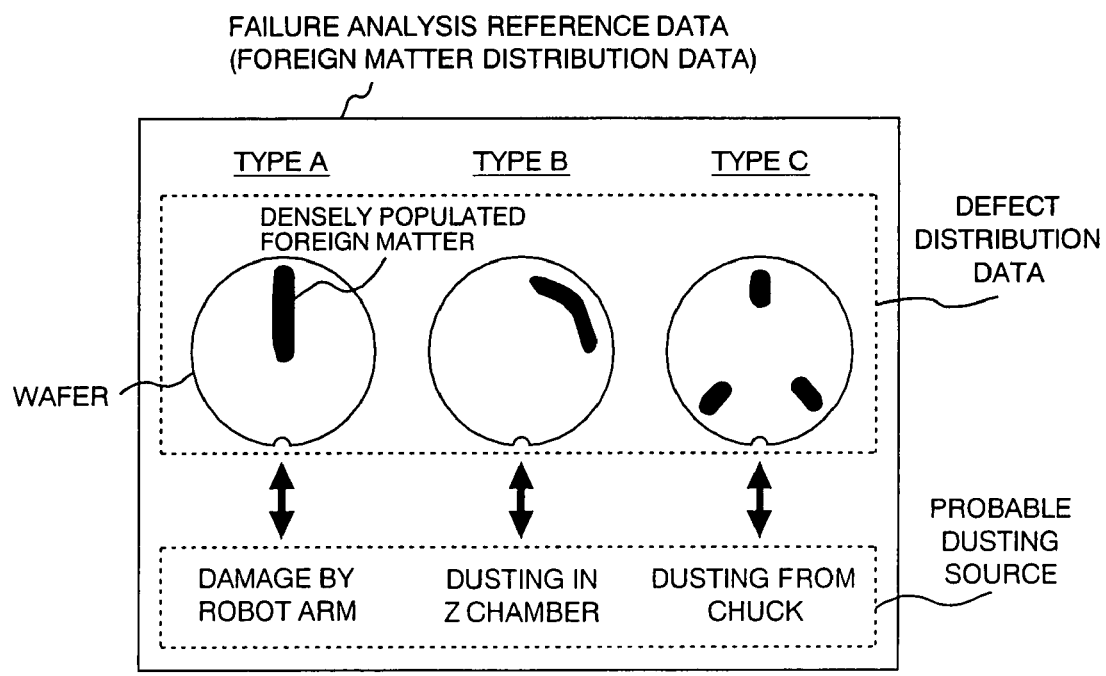
FIG. 26 is an example of failure analysis reference data.

In the database 251, failure analysis reference data (foreign matter distribution data) such as shown in FIG. 26 are prepared. For example, type A may be attributable to damage by a robot arm, type B to dusting in chamber Z and type C to dusting from a chuck.

FIG. 27 shows a result of analysis by the data analysis processing unit 230. Indicated are defect distributions detected by the image signal processing unit 210 in wafers after or before manufacture process CCC is applied to these wafers set in slots 1 through 5 in process processing apparatus AAA. The wafers belongs to product type BBB and lot No. DDD. As a result of analysis, an alarm 271 is output to indicate that abnormal defects are found in a wafer set in slot 5 and they may be attributable to damage by a robot arm.

Figure 28:
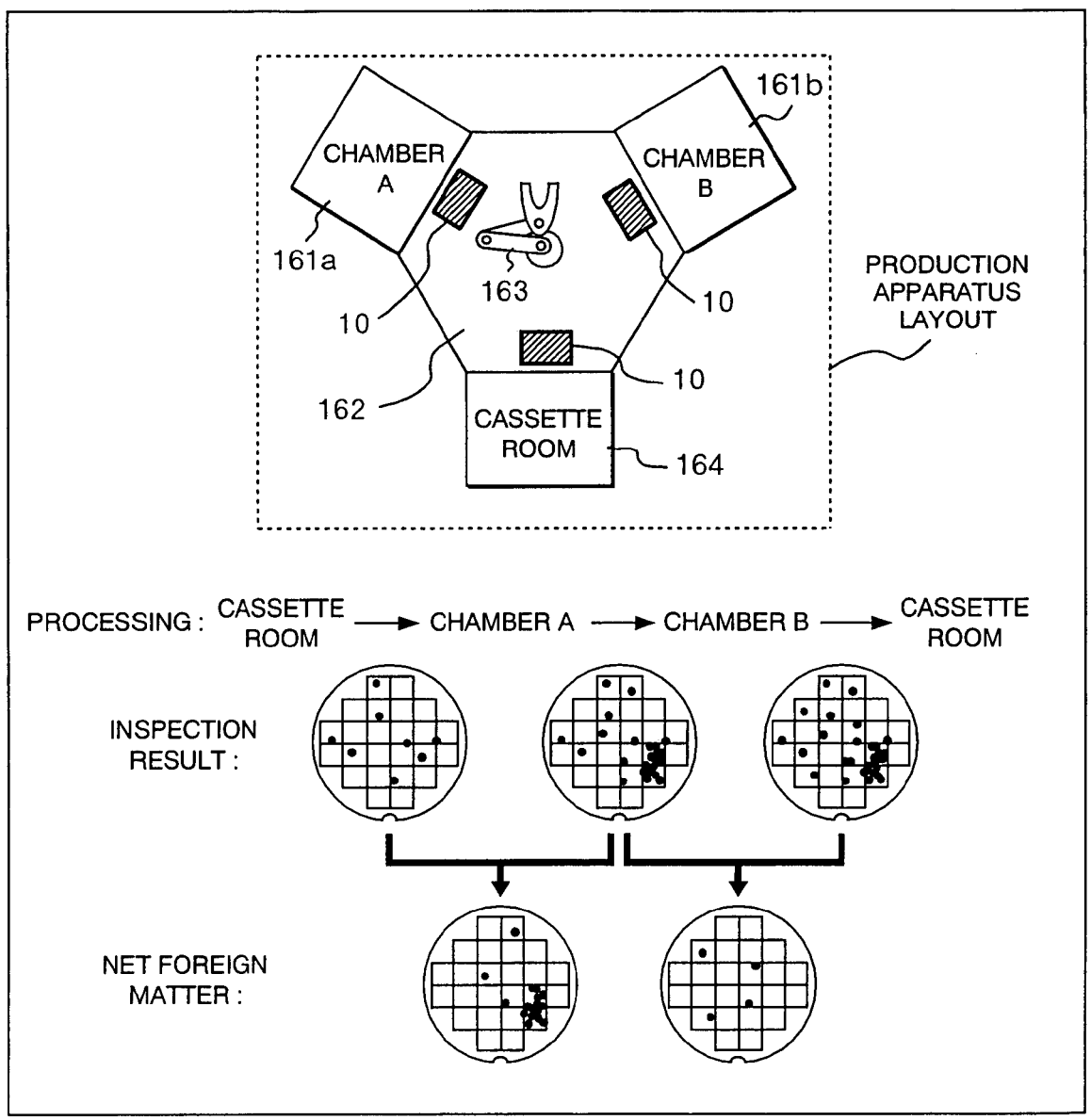
FIG. 28 shows net foreign matter distributions obtained by compact foreign matter monitors set up respectively for chambers.

Shown in FIG. 28 are inspection results obtained from the image signal processing unit 210 and analysis results (net foreign matters) by data analysis processing unit 220 when compact foreign matter monitors 10 are set up respectively in a platform 162 for a cassette room 164, chamber A 161a and chamber B 161b in a process processing apparatus. From these net foreign matter distributions, it is found that chamber A is dusting.

Figure 29:
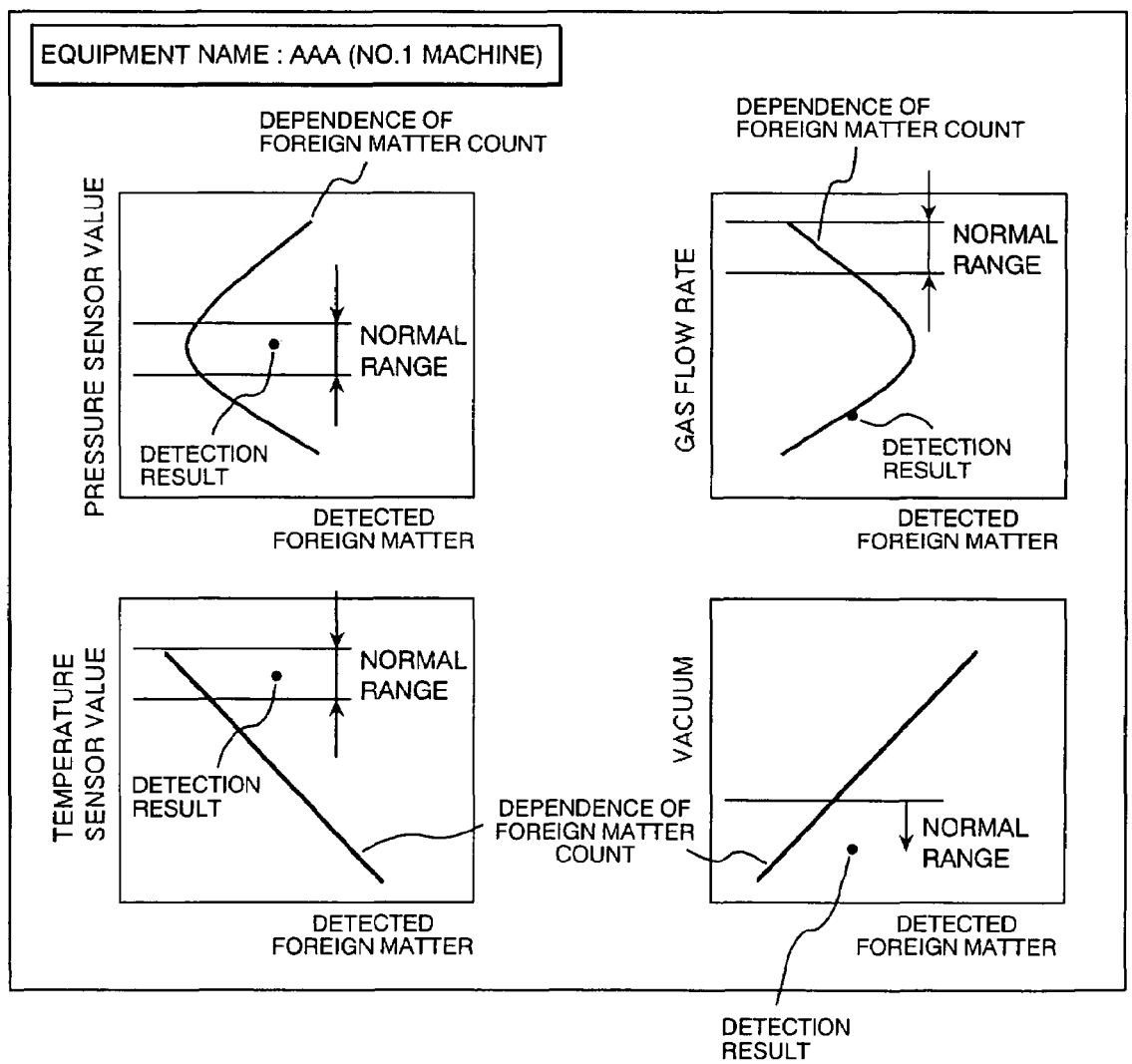
FIG. 29 shows how the number of foreign matters depends on respective parameters (pressure sensor value, temperature sensor value, gas flow rate and degree of vacuum)

If the relations of the number of foreign matters per wafer with the gas pressure, supplied gas flow rate, temperature and degree of vacuum are stored as part of the failure analysis reference data in the database 251 for each of process chambers 151, 161, 181 and 191 in a process processing apparatus which may generate foreign matters, it is possible to find a probable cause of a large number of foreign matters according to the gas pressure, supplied gas flow rate, temperature and degree of vacuum measured in chambers 151, 161, 181 and 191 while wafers were scanned. In FIG. 29, the measured gas pressure, temperature and degree of vacuum are in the respective normal ranges and the large number of foreign matters are attributable to the gas flow rate.

Figure 30:
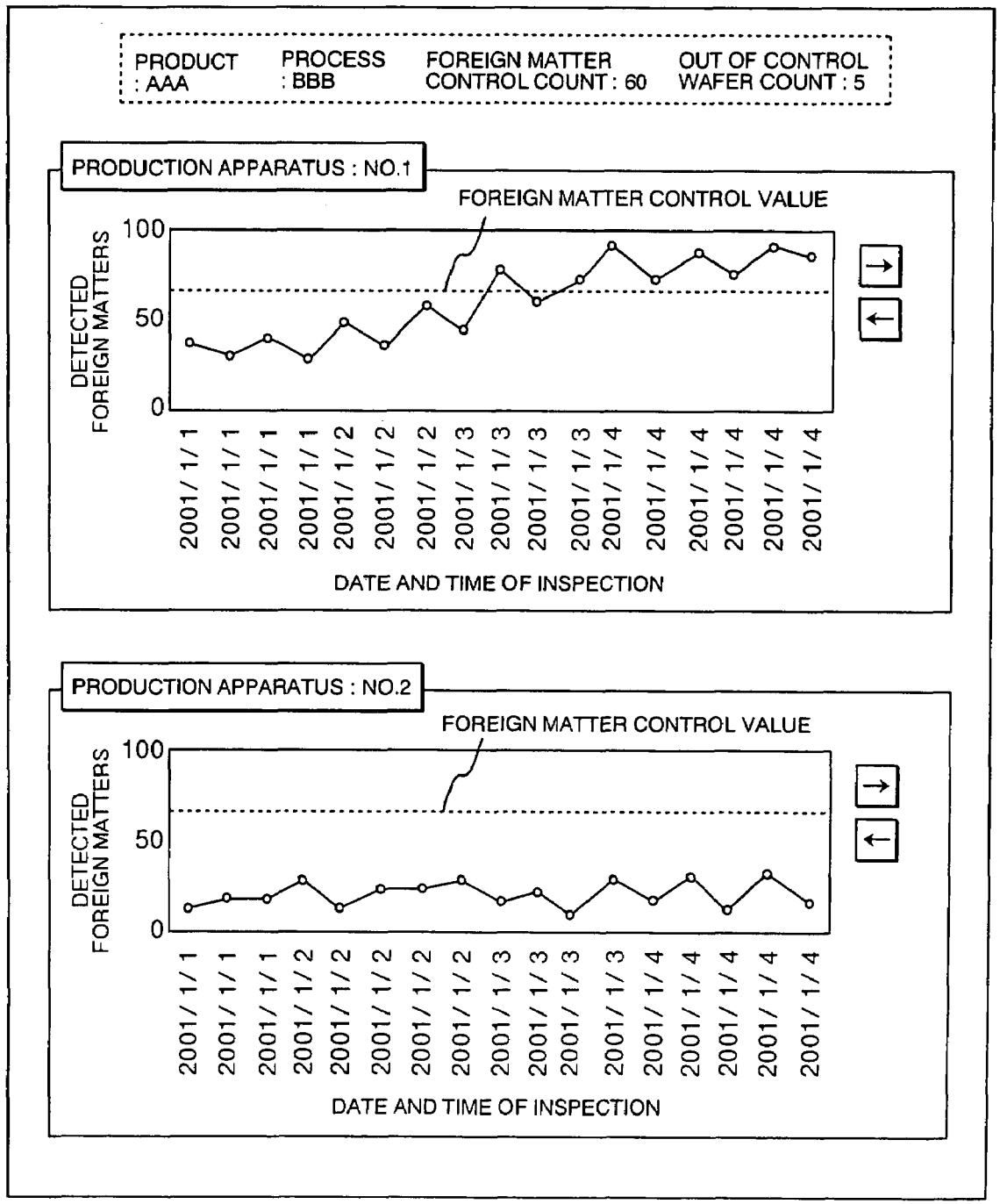
FIG. 30 shows a screen indicating in detail how the number of foreign matters detected in each process processing apparatus changed with time.
Figure 31:
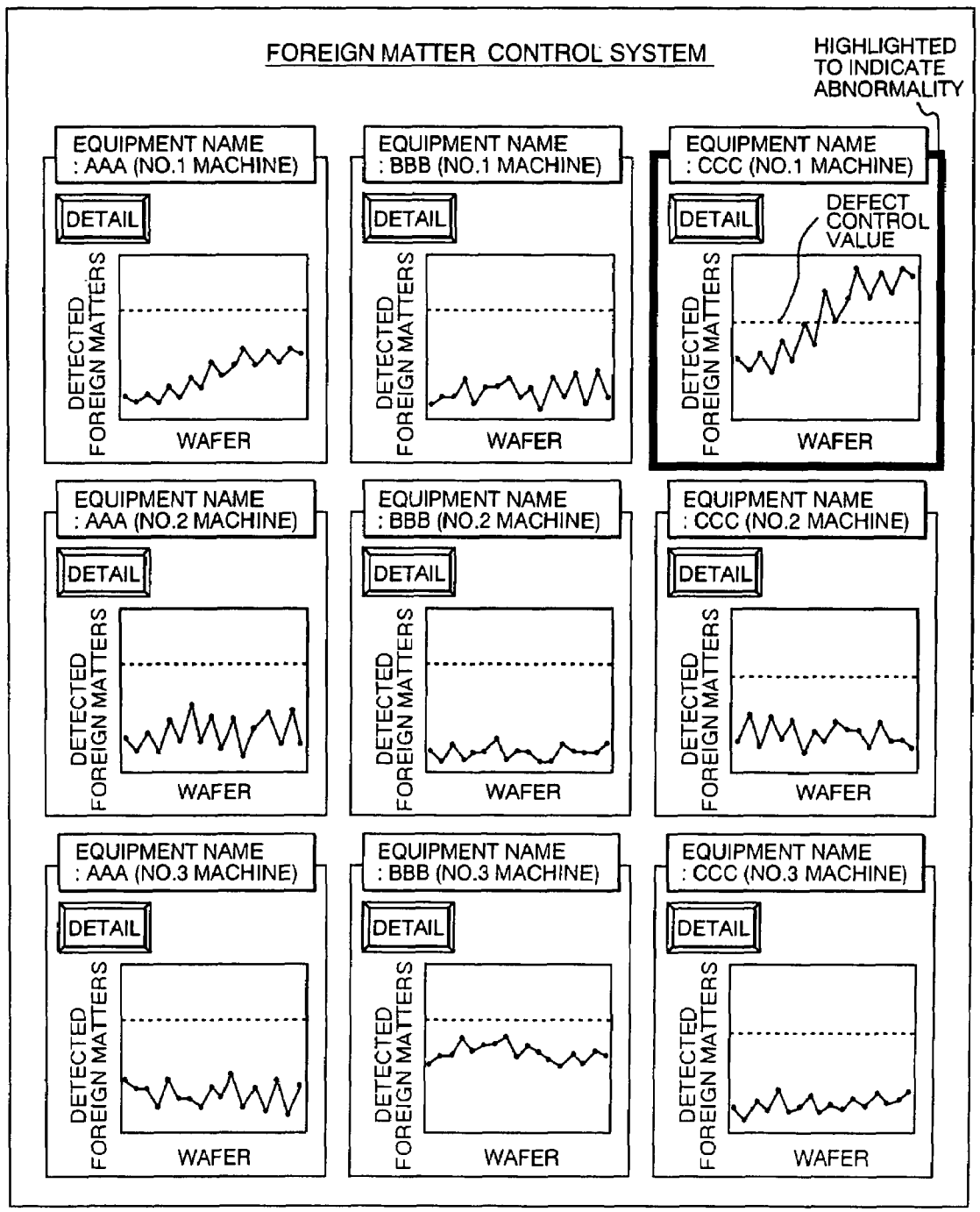
FIG. 31 shows a screen designed to cover more process processing apparatuses than in the screen of FIG. 30 and allow switching to a detailed format.

FIG. 30 shows a screen displayed on the input/output terminal by the data analysis processing unit 220. The number of foreign matters detected in one of every five wafers in each process processing apparatus is plotted at each inspection date. Accordingly, if the number of foreign matters detected in one of every five wafers in a process processing apparatus becomes likely to exceed the foreign matter control value, the data analysis processing unit 220 may notify of this situation and issue an alarm to the process processing apparatus. For example, if the number of wafers having more foreign matters than the foreign matter control value (the number of out of control wafers) has reached to 5, the data analysis processing unit 220 notifies of this situation and issues an alarm to the process processing apparatus. In the case of a screen shown in FIG. 31, more process processing apparatuses are covered. Changes in the number of foreign matters detected per wafer in many process processing apparatuses are respectively displayed on the input/output terminal 260 by the data analysis processing unit 220. This screen can indicate more abnormal process processing apparatuses in which the number of detected foreign matters is going to exceed the control value.

In addition, if the correlation of the number of detected foreign matters and the yield is stored as part of the failure analysis reference data in the database 251, it is possible to predict the total yield of the manufacture line since the number of foreign matters detected in each process of the manufacture line can be grasped by the data analysis processing unit 220. Anyway, the base system 20 obtains yield information from the electric inspection system 50. In addition, information generated by offline inspection/analysis can be collected to the base system 20 from the measuring device group 40.

When the base system 20 cannot be connected to an external system, the input/output terminal 260 is used to input and output information.

Then an example of implementing electronic trade by using compact foreign matter monitors 10 as on-machine monitors according to the present invention as described so far will be described. Mounting compact foreign matter monitors 10 in many process processing apparatuses as on-machine monitors makes the manufacture line very expensive. Therefore, compact foreign matter monitors 10 are leased to a device manufacturer 500 or a production apparatus manufacturer 520 free of charge or at a low rate. Since the base system 20 can always monitor the manufacture line to check if foreign matters occur through compact foreign matter monitors 10a through 10n mounted in major process processing apparatuses Pa through Pn constituting the manufacture line, it is possible to immediately take measures aimed at improving the yield.

Figure 32:
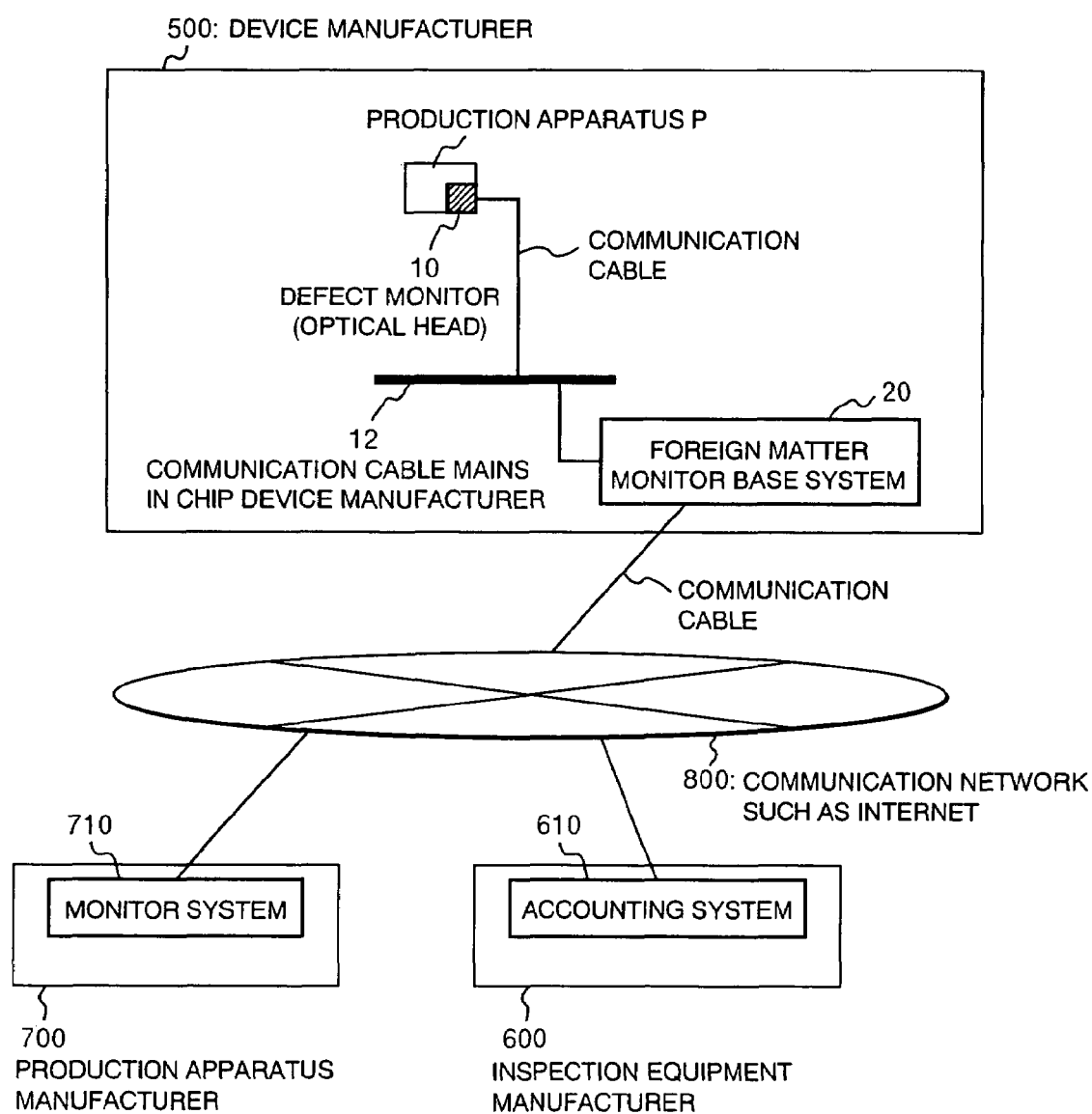
FIG. 32 shows a hardware configuration to implement an electronic transaction method using a foreign matter monitoring system according to the present invention.

FIG. 32 describes the general configuration of this embodiment. A base system 20 set up in a device manufacturer 500, an accounting system 610 set up in an inspection equipment manufacturer 600 and a monitor system 710 set up in a production apparatus manufacturer 700 are connected via a communication network 800.

The device manufacturer 500 requests the inspection equipment manufacturer 600 to lease a compact foreign matter monitor 10 via the network 800 and contracts with the inspection equipment manufacturer 600. The device manufacturer 500 requests the manufacturer 700 of the process processing apparatus P to set up a compact foreign matter monitor in the process processing apparatus P and contracts with the production apparatus manufacturer 700. The inspection equipment manufacturer 600 leases and sets up the compact foreign matter monitor 10 for the device manufacturer 500. This results in compact foreign matter monitors 10a through 10n mounted on process processing apparatuses Pa through Pn as on-machine monitors. After it is verified through inspection over a certain period that they are free from abnormality, how to calculate the amount of payment for inspection is determined between the device manufacturer 500 and the inspection equipment manufacturer 600. After this, the compact foreign matter monitors 10a through 10n are put to regular use and the base system 20 always monitors the manufacture line to check if foreign matters occur abnormally and performs feedback so that measures can be taken if necessary. As a result, the yield can be improved as an economic effect by inspection. Accordingly, the device manufacturer 500 pays money in the accounting system 610 of the inspection equipment manufacturer 600 for the economic effect (increase in the yield) by inspection.

Figure 33:
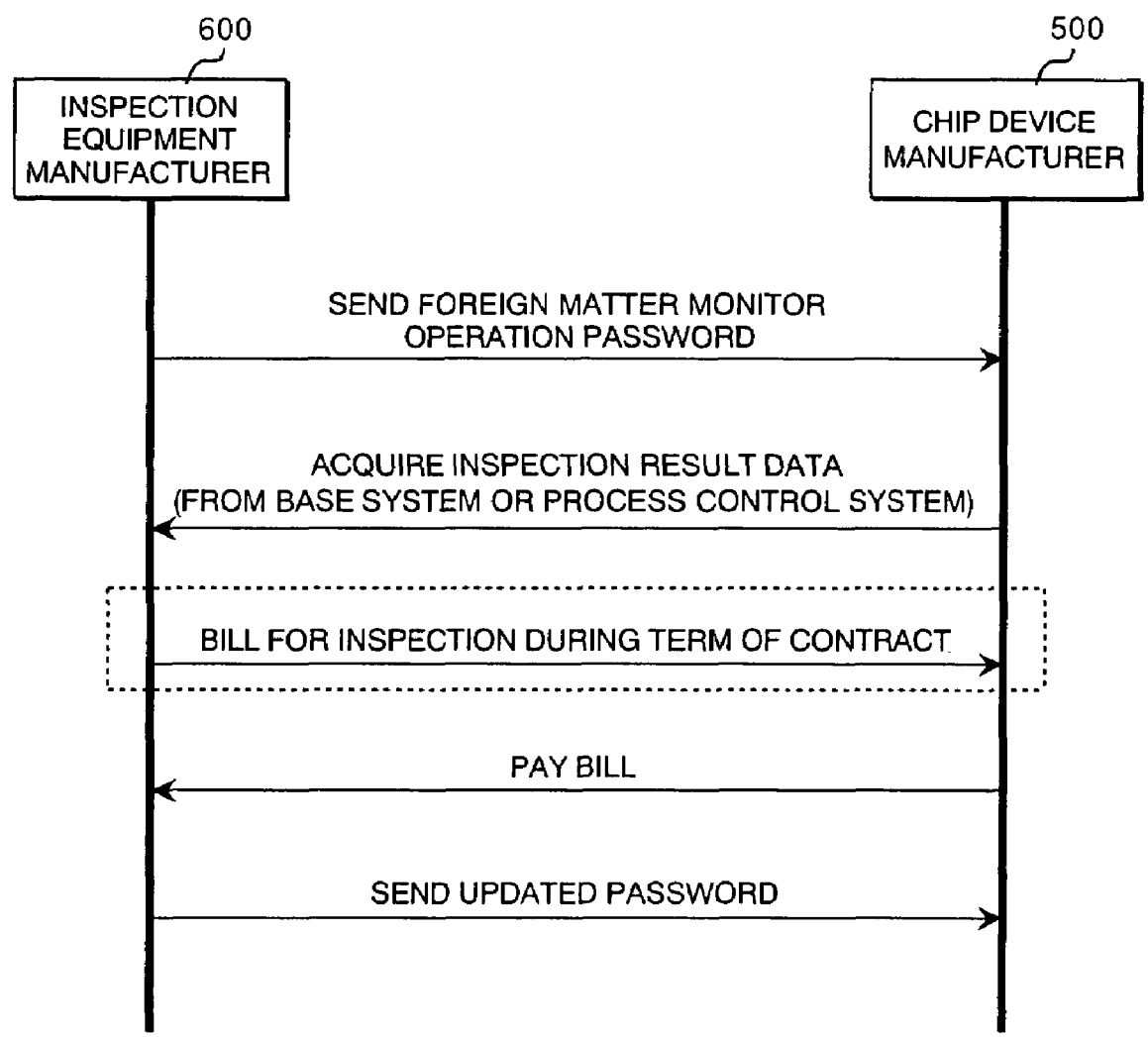
FIG. 33 is a diagram for explaining a basic sequence in an electronic transaction method (a method of electronic commerce) according to the present invention.

Then, an example of a sequence in which the inspection equipment manufacturer 600 demands payment from the device manufacturer 500 will be described with reference to FIG. 33. The accounting system 610 of the inspection equipment manufacturer 600 sends a foreign matter monitor operation password to the base system 20 or production management system 30 of the device manufacturer 500. As a result, the accounting system 610 is notified by the base system 20 or production management system 30 of the economic effect (increase in the yield) brought about by inspection and, based on this, demands payment for inspection over the term of contract (one month or year). The device manufacturer 610 pays the demanded amount of money in the accounting system 610 which in turn sends an updated password to the base system 20 or production management system 30.

Figure 34:
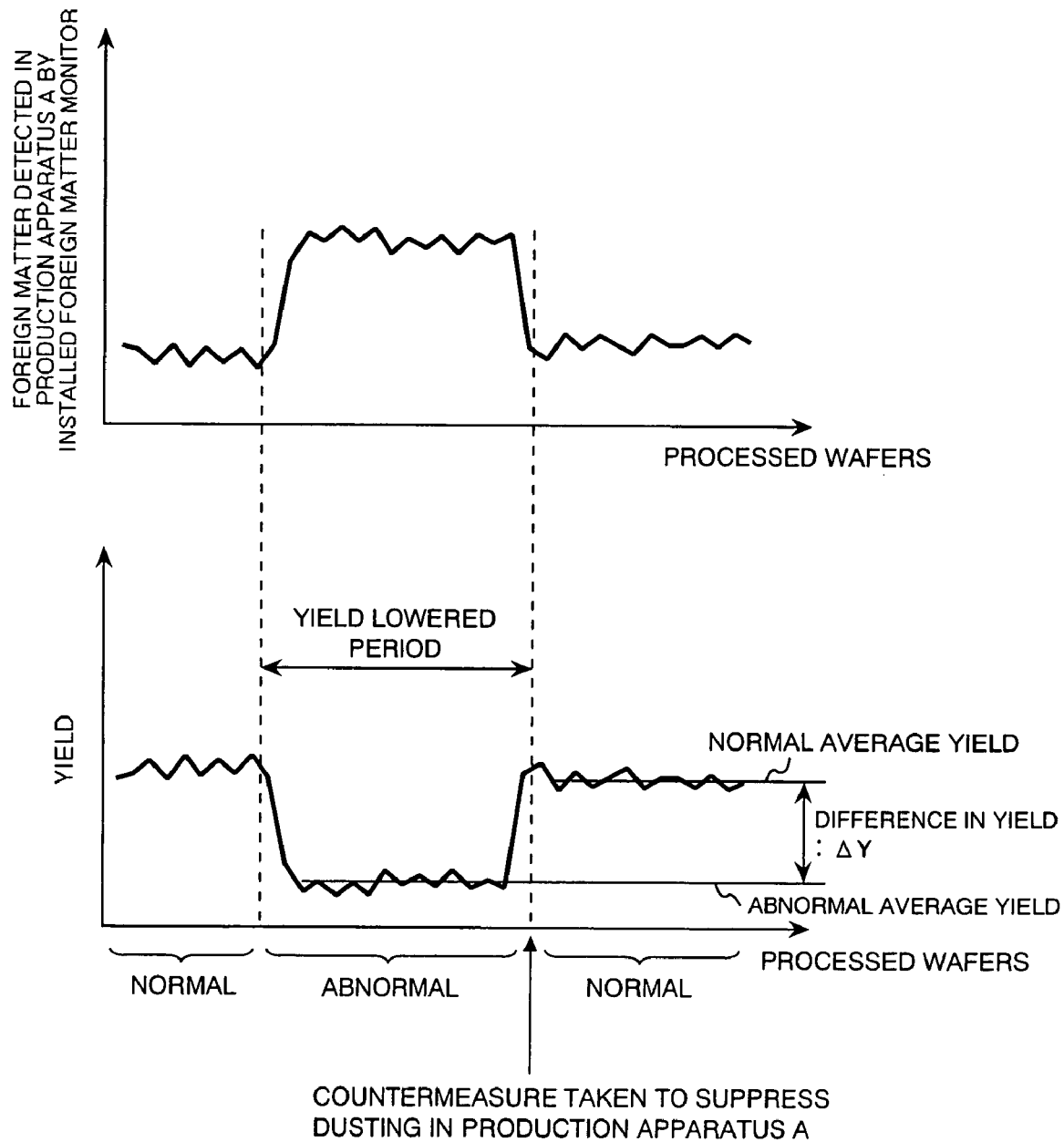
FIG. 34 is a diagram for explaining a first example of how to calculate the amount of money to be paid for inspection in an electronic transaction method according to the present invention.

Then a first example of how to calculate the amount of money to be paid for inspection will be described with reference to FIG. 34. Economic effect E by foreign matter monitors is expressed by Equation (1) as below:

$$E = m \times \Delta Y \times V \times k \quad (1)$$

where, m is the number of wafers processed in a low yield period, $\Delta Y$ is a difference in the yield, V is the unit wafer price and k is a coefficient. For example, m equals (average dusting period in manufacture apparatus A, regular foreign matter QC interval or time left until the next regular QC)×(average number of wafers processed per hour). V equals (chip manufacture cost)×(number of chips yielded per wafer).

Figure 35:
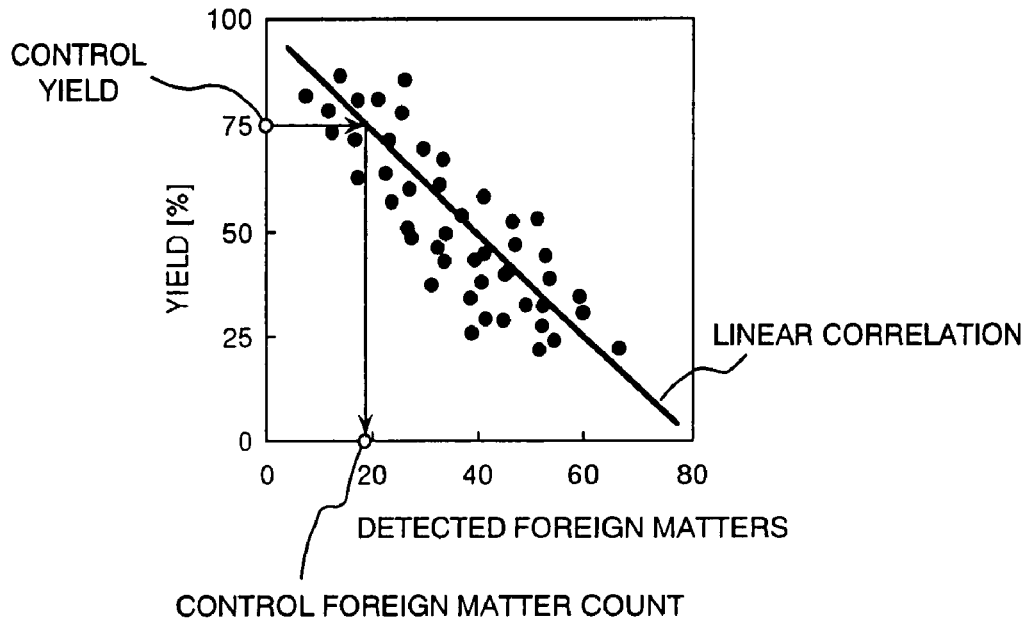
FIG. 35 is a diagram for explaining a second example of how to calculate the amount of money to be paid for inspection in an electronic transaction method according to the present invention.

Then, a second example of how to calculate the amount of money to be paid for inspection will be described with reference to FIG. 35. In short, a control foreign matter count is determined from a linear correlation between the number of detected foreign matters and the yield jointly by the inspection equipment manufacturer 600 and device manufacturer 500. If the number of detected foreign matters, reported as an inspection result from the device manufacturer 500, exceeds the predetermined control foreign matter count, the inspection equipment manufacturer 600 sends an alarm to the device manufacturer and demands payment for instruction. Instead of the number of detected foreign matters, the judgment may also be based on the number of foreign matters beyond a certain size, the density of foreign matters, the distribution of foreign matters or the like. Note that the yield-related data are obtained from the electric inspection system 50.

Figure 36:
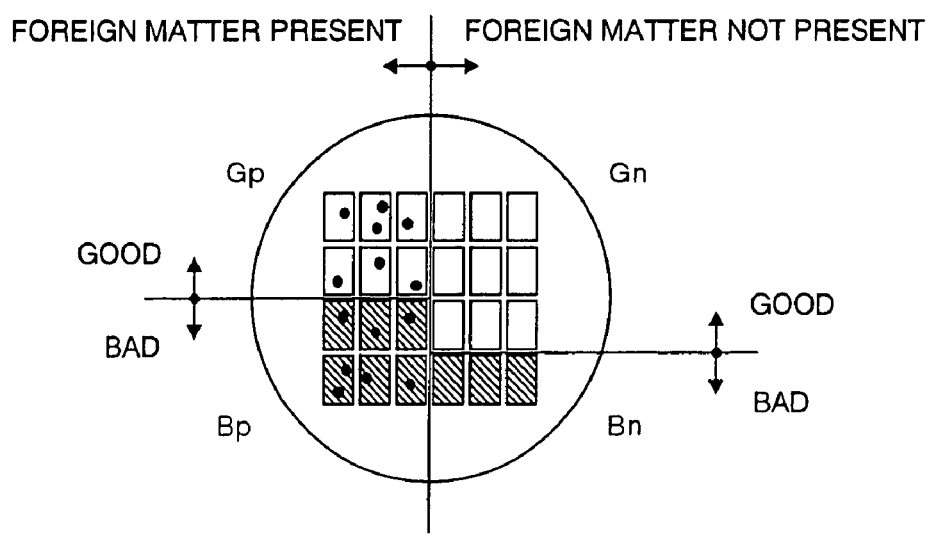
FIG. 36 is a diagram for explaining a third example of how to calculate the amount of money to be paid for inspection in an electronic transaction method according to the present invention.
Figure 37:
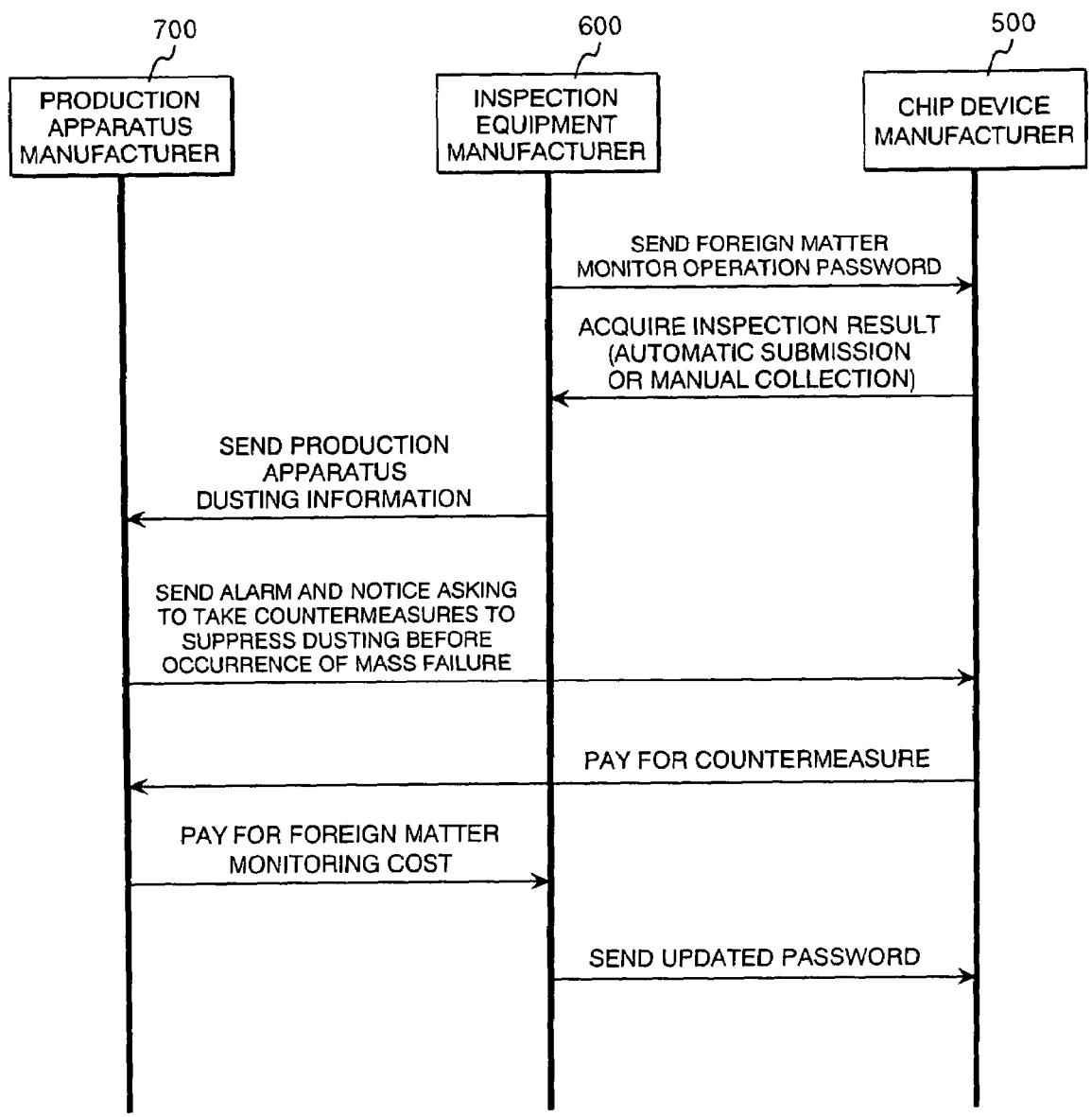
FIG. 37 is a diagram for explaining how payment is demanded to a production apparatus manufacturer in an electronic transaction method according to the present invention.

Then, a third example of how to calculate the amount of money to be paid for inspection will be described with reference to FIG. 36. In the third example, the amount of money to be paid for inspection is calculated according to yield influence dY instead of the yield. Using yield influence dY makes it possible to accurately estimate the influence of foreign matters in the pertinent process processing apparatus. By representing the yield of foreign matter present chips as Yp, the yield of chips free from foreign mater as Yn, the ratio of foreign matter detected chips to all chips as γ and the probability of a chip failing due to foreign matter as F, yield influence dY is expressed by Equation (2) as below:

$$dY = Yn \times F \times \gamma \quad (2)$$

where, Y=(Gn+Gp)/(Gn+Bn+Gp+Bp),
Yn=Gn/(Gn+Bn),
Yp=Gp/(Gp+Bp),
γ=(Gp+Bp)/(Gn+Bn+Gp+Bp) and
F=1−(Yp/Yn)

Then, an example of a sequence in which a production apparatus manufacturer is demanded to pay for cost will be described. The accounting system 610 of an inspection equipment manufacturer 600 sends a foreign monitor operation password to the base system 20 or production management system 30 of a device manufacturer 500. As a result, the accounting system 610 collects dusting information about process processing apparatuses as inspection results from the base system 20 or production management system 30, and sends the dusting information about the process processing apparatuses to the monitor system 710 of the manufacturer 700 of the process processing apparatuses. The monitor system 710 issue an alarm and notice to the base system 20 or production management system 30 of the device manufacturer 500 in order to notify of countermeasures which must be taken to suppress dusting for preventing mass failure and demands payment for this consultancy. The device manufacturer 500 pays the demanded amount of money to the production apparatus manufacturer 700. The production apparatus manufacturer 700 pays to the accounting system 610 of the inspection equipment manufacturer 600 for the foreign matter monitoring cost. The accounting system 610 of the inspection equipment manufacturer 600 sends an updated password to the base system 20 or production management system 30 of the device manufacturer 500.

In this configuration, the production apparatus manufacturer 700 can sell dusting check-guaranteed production apparatus to the device manufacturer 500 and consequently can be paid for anti-dusting countermeasures. The inspection equipment manufacturer 600 can also be paid for the foreign matter monitoring cost. In addition, the device manufacturer 500 can use process processing apparatuses P without uneasiness since anti-dusting countermeasure service is guaranteed.

Figure 38:
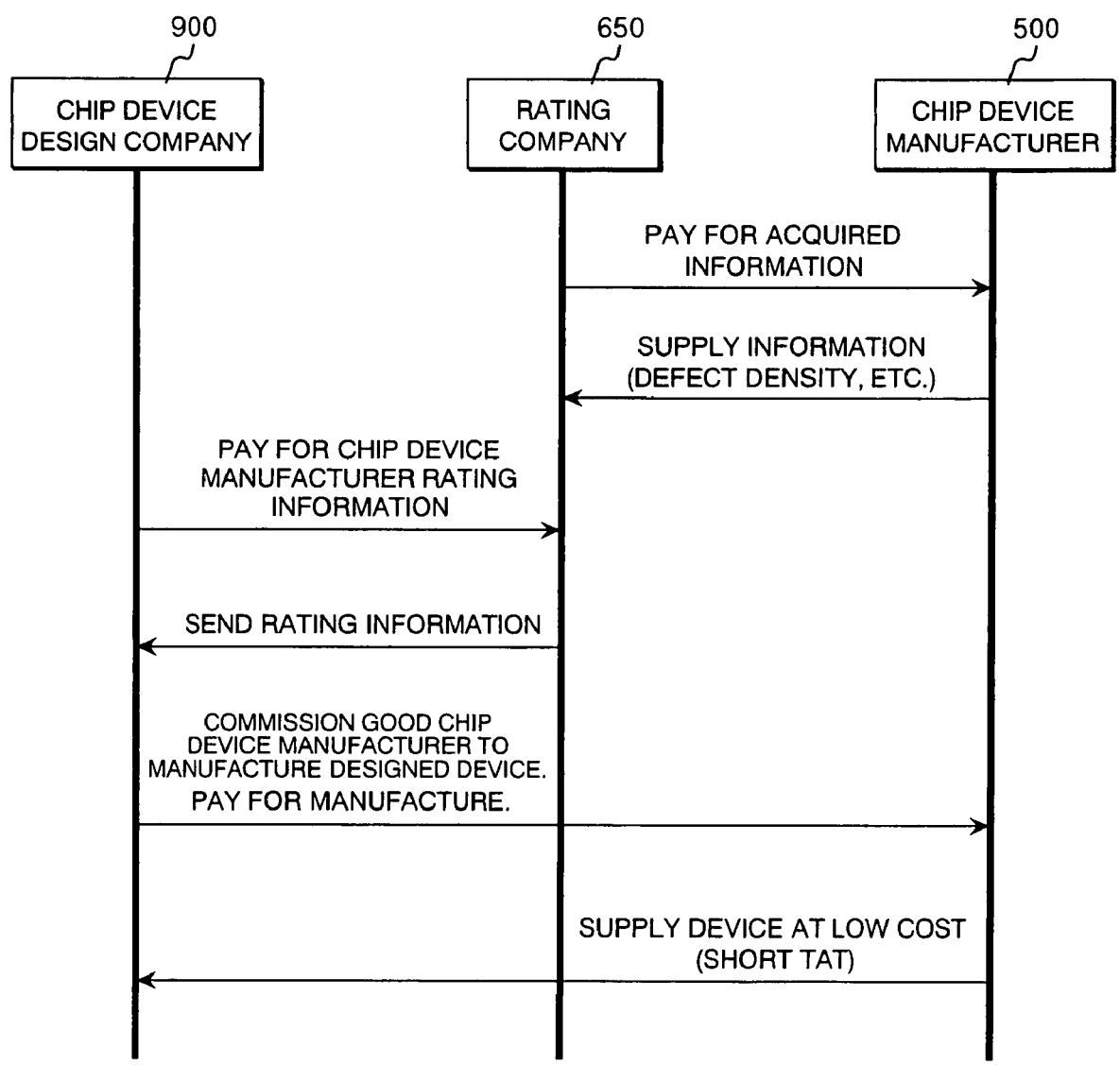
FIG. 38 is a diagram for explaining how rating service is provided by a rating company (for example, an inspection equipment manufacturer) in an electronic transaction method according to the present invention.
Figure 39:
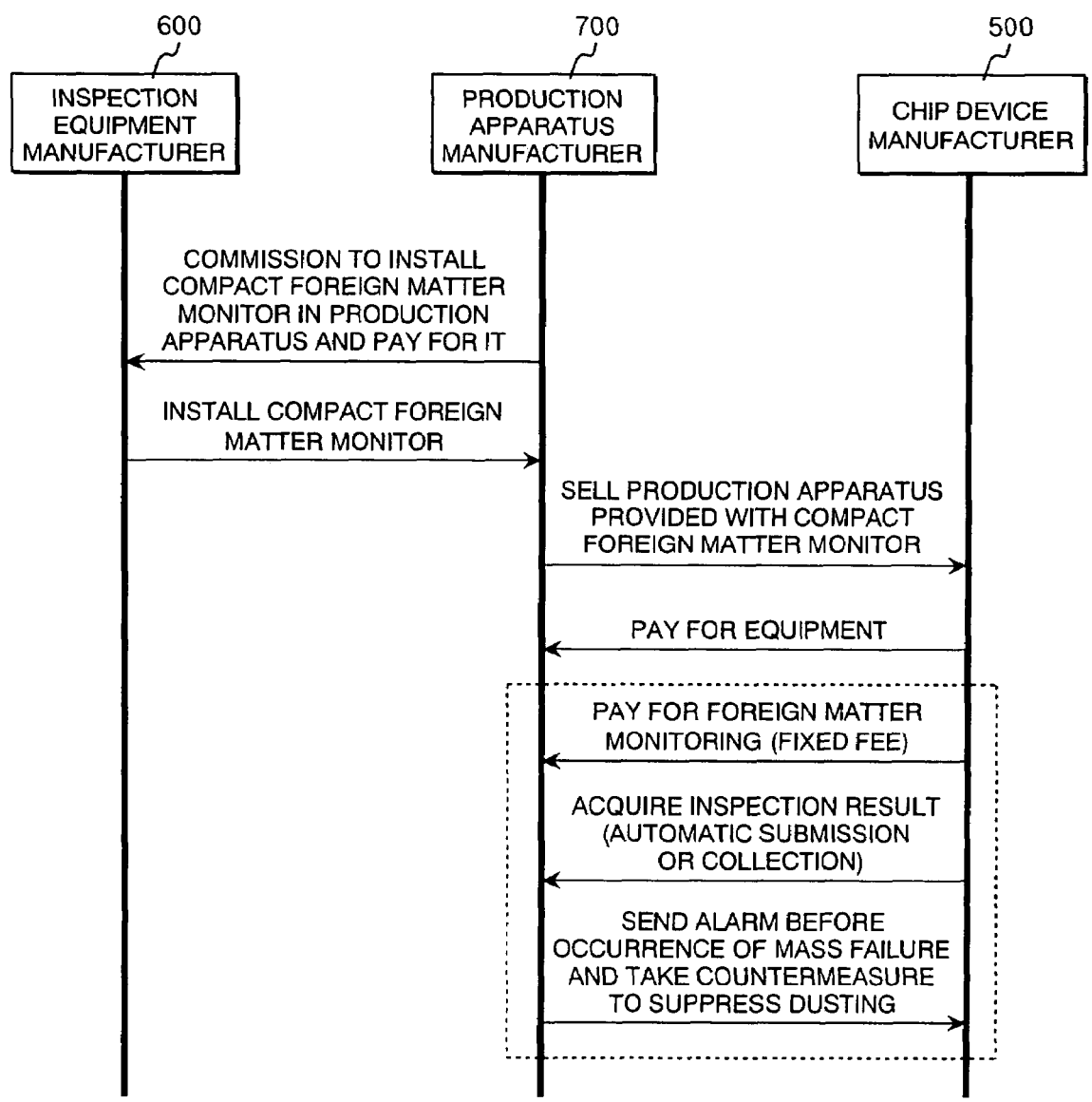
FIG. 39 is a diagram for explaining how a production apparatus manufacturer initiatively demands payment in an electronic transaction method according to the present invention.

Then, an example of a sequence in which rating service is provided by a rating company (inspection equipment manufacturer) will be described with reference to FIG. 38. Firstly, the rating company 650 pays to a device manufacturer 500 for information collecting. Consequently, the device manufacturer 500 provides information, such as the number of foreign matters, density of defects and yield, to the rating company 650. Then, a chip design company 900 pays to the rating company 600 for acquiring rating information about device manufacturers. Consequently, the rating company 600 encrypted rating information to the chip design company 900. Encryption intends to prevent the sent information from being misappropriated. As a result of this sequence, the device design manufacturer 900 commissions a good device manufacturer to manufacture a designed device and pays for the manufacture.

As described above, since the rating company 650 acquires high reliability information, such as the number of foreign matters and yield, from device manufacturers, and provides the information to the device design company 900, the device design company 900 can obtain chips manufactured according to a design from a device manufacturer at low cost (in short TAT). The rating company 650 can take an intermediate margin. If the inspection equipment manufacturer 600 serves as a rating company 650, sale of its own equipment may be promoted. In addition, the device manufacturer 500 can make a profit by receiving orders for manufacturing devices.

Then an example of a sequence in which a production apparatus manufacturer takes the initiative will be described. A production apparatus manufacturer 700 commissions an inspection equipment manufacturer 600 to mount a compact foreign matter monitor 10 in a process processing apparatus P and pays for the mounting. Then, the process processing apparatus P in which the compact foreign matter monitor 10 purchased from the inspection equipment manufacturer 600 is mounted is sold by the production apparatus manufacturer 700 to a device manufacturer 500 as a compact foreign matter monitor-integrated production apparatus. The device manufacturer 500 pays for the apparatus. The production apparatus manufacturer 700 collects a fixed amount of money (for a certain period) for the monitoring cost from the device manufacturer 500. Then, the production apparatus manufacturer 700 is notified by the base system 20 of inspection results and, based on the inspection results, performs failure analysis. As necessary, the production apparatus manufacturer 700 issues an alarm to the device manufacturer 500 and takes anti-dusting countermeasures to prevent mass failure.

Figure 40:
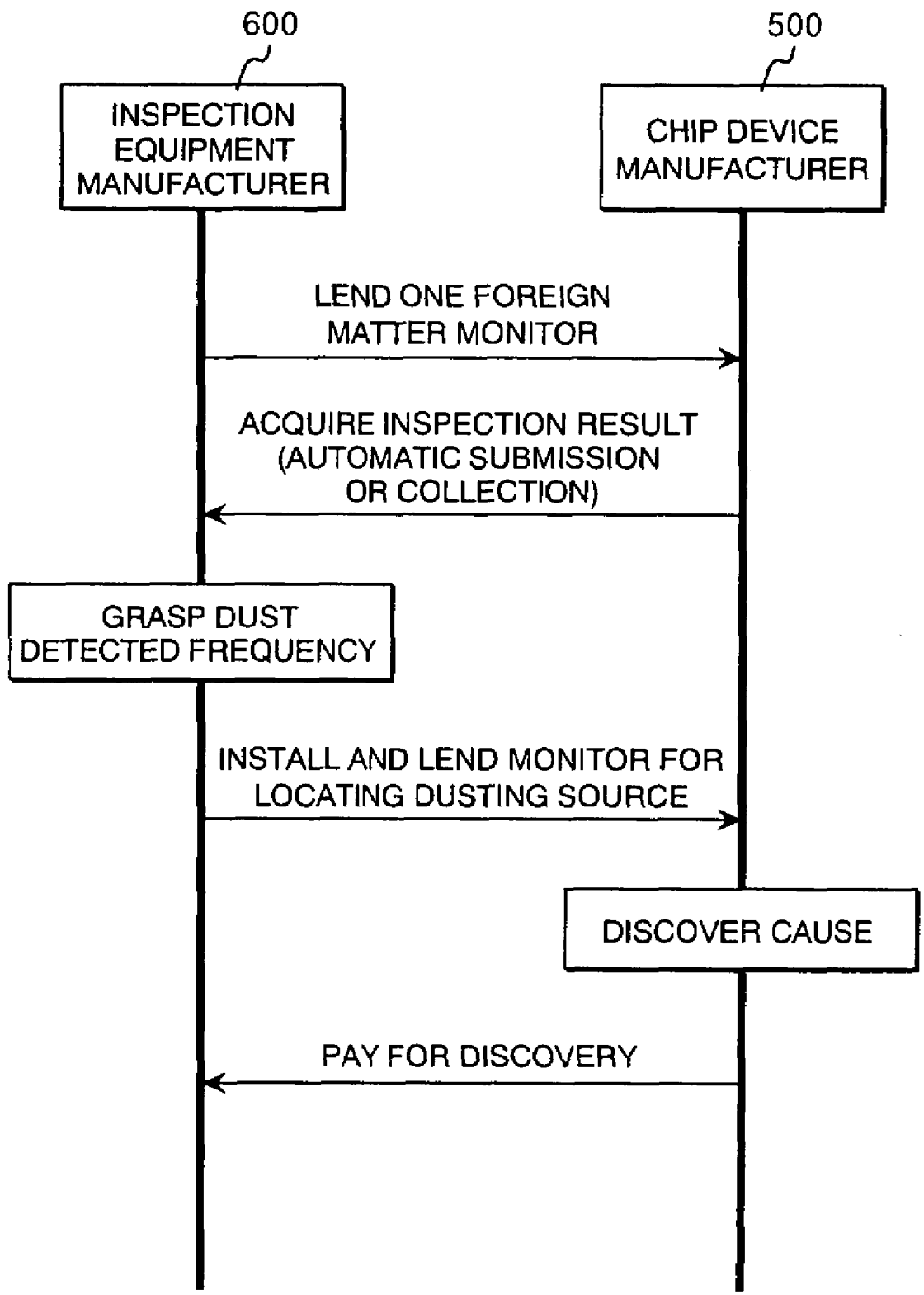
FIG. 40 is a diagram for explaining how a compact foreign matter monitor (optical head) is added in an electronic transaction method according to the present invention.

Then, an example of a sequence in which a compact foreign matter monitor (optical head) is added will be described with reference to FIG. 40. An inspection equipment manufacturer 600 leases one or plural compact foreign matter monitors 10 to a device manufacturer 500 and acquires results of foreign matter monitoring inspection from the base system 20 of the device manufacturer 500 to grasp the dusting frequency. If necessary, the inspection equipment manufacturer 600 leases another compact foreign matter monitor to the device manufacturer 500. This added compact foreign matter monitor is used by the device manufacturer 500 to locate the dusting source. The device manufacturer 500 pays to the inspection equipment manufacturer 600 for the troubleshooting.

What is claimed is:

1. A system for monitoring foreign matter comprising:
   a manufacturing line having plural process processing apparatuses;
   a production management system which manages the processing of workpieces in the manufacturing line;
   plural optical heads which monitor foreign matter in relation to at least one of the workpieces, and which provide an output signal indicative thereof; and
   at least one image signal processing unit provided in a lesser number than a number of the plural optical heads for processing the output signal therefrom.

2. A system for monitoring foreign matter according to claim 1, wherein only a single image processing unit is provided.

3. A system for monitoring foreign matter according to claim 1, wherein each of the optical heads contain an illuminating optical system for irradiating at least one of the workpieces in a respective one of the plural process processing apparatuses with light and a detecting optical system for receiving reflected and scattered light from the at least one of the workpieces and for converting the received light to a detection image signal as the output signal from the optical head.

* * * * *

UNITED STATES PATENT AND TRADEMARK OFFICE
CERTIFICATE OF CORRECTION

PATENT NO. : 7,499,157 B2  Page 1 of 1
APPLICATION NO. : 11/727037
DATED : March 3, 2009
INVENTOR(S) : Nishiyama et al.

It is certified that error appears in the above-identified patent and that said Letters Patent is hereby corrected as shown below:

On the title page, item (73) should read:

(73) Assignee: Hitachi High-Technologies Corporation, Tokyo (JP)

Signed and Sealed this

Seventeenth Day of November, 2009

David J. Kappos
*Director of the United States Patent and Trademark Office*